US008207232B2

(12) United States Patent
Babcock et al.

(10) Patent No.: US 8,207,232 B2
(45) Date of Patent: Jun. 26, 2012

(54) PHARMACEUTICAL COMPOSITIONS WITH ENHANCED PERFORMANCE

(75) Inventors: Walter C. Babcock, Bend, OR (US); Dwayne T. Friesen, Bend, OR (US); David Keith Lyon, Bend, OR (US); Warren Kenyon Miller, Bend, OR (US); Daniel Tod Smithey, Bend, OR (US)

(73) Assignee: Bend Research, Inc., Bend, OR (US)

( * ) Notice: Subject to any disclaimer, the term of this patent is extended or adjusted under 35 U.S.C. 154(b) by 1039 days.

(21) Appl. No.: 11/569,433

(22) PCT Filed: May 18, 2005

(86) PCT No.: PCT/IB2005/001580
§ 371 (c)(1),
(2), (4) Date: May 23, 2008

(87) PCT Pub. No.: WO2005/115330
PCT Pub. Date: Dec. 8, 2005

(65) Prior Publication Data
US 2008/0262107 A1  Oct. 23, 2008

Related U.S. Application Data

(60) Provisional application No. 60/575,541, filed on May 28, 2004, provisional application No. 60/586,549, filed on Jul. 9, 2004.

(51) Int. Cl.
*A61K 47/38* (2006.01)
*A61K 9/00* (2006.01)
*A61K 9/10* (2006.01)

(52) U.S. Cl. .......... 514/781; 424/400; 424/488
(58) Field of Classification Search .......... None
See application file for complete search history.

(56) References Cited

U.S. PATENT DOCUMENTS

| 4,226,981 | A | * | 10/1980 | Onda et al. ............ 536/66 |
| 4,385,078 | A | * | 5/1983 | Onda et al. ............ 427/2.21 |
| 5,700,929 | A | * | 12/1997 | Kokubo et al. ............ 536/63 |
| 5,776,501 | A | | 7/1998 | Kokubo et al. |
| 6,548,555 | B1 | * | 4/2003 | Curatolo et al. ............ 514/772.4 |

FOREIGN PATENT DOCUMENTS

| EP | 0344603 B1 | 10/1991 |
| EP | 1027886 B1 | 7/2008 |
| WO | 03/063822 A2 | 8/2003 |
| WO | 20051020929 A2 | 3/2005 |

OTHER PUBLICATIONS

M. Fukasawa and S. Obara, "Molecular Weight Determination of Hypromellose Acetate Succinate (HPMCAS) Using Size Exclusion Chromotography with a Multi-Angle Laser Light Scattering Detector", Chem. Pharm Bull. 52(11) 1391-1393, 2004.

* cited by examiner

*Primary Examiner* — Ernst Arnold
*Assistant Examiner* — Christopher R Lea
(74) *Attorney, Agent, or Firm* — Chernoff, Vilhauer, McClung & Stenzel

(57) ABSTRACT

Disclosed are polymers of hydroxypropyl methyl cellulose acetate succinate (HPMCAS) and hydroxypropyl methyl cellulose acetate (HPMCA) with unique degrees of substitution of hydroxypropoxy, methoxy, acetyl, and succinoyl groups. When used in making compositions comprising a low-solubility drug and such polymers, the polymers provide enhanced aqueous concentrations and/or improved physical stability.

9 Claims, 1 Drawing Sheet

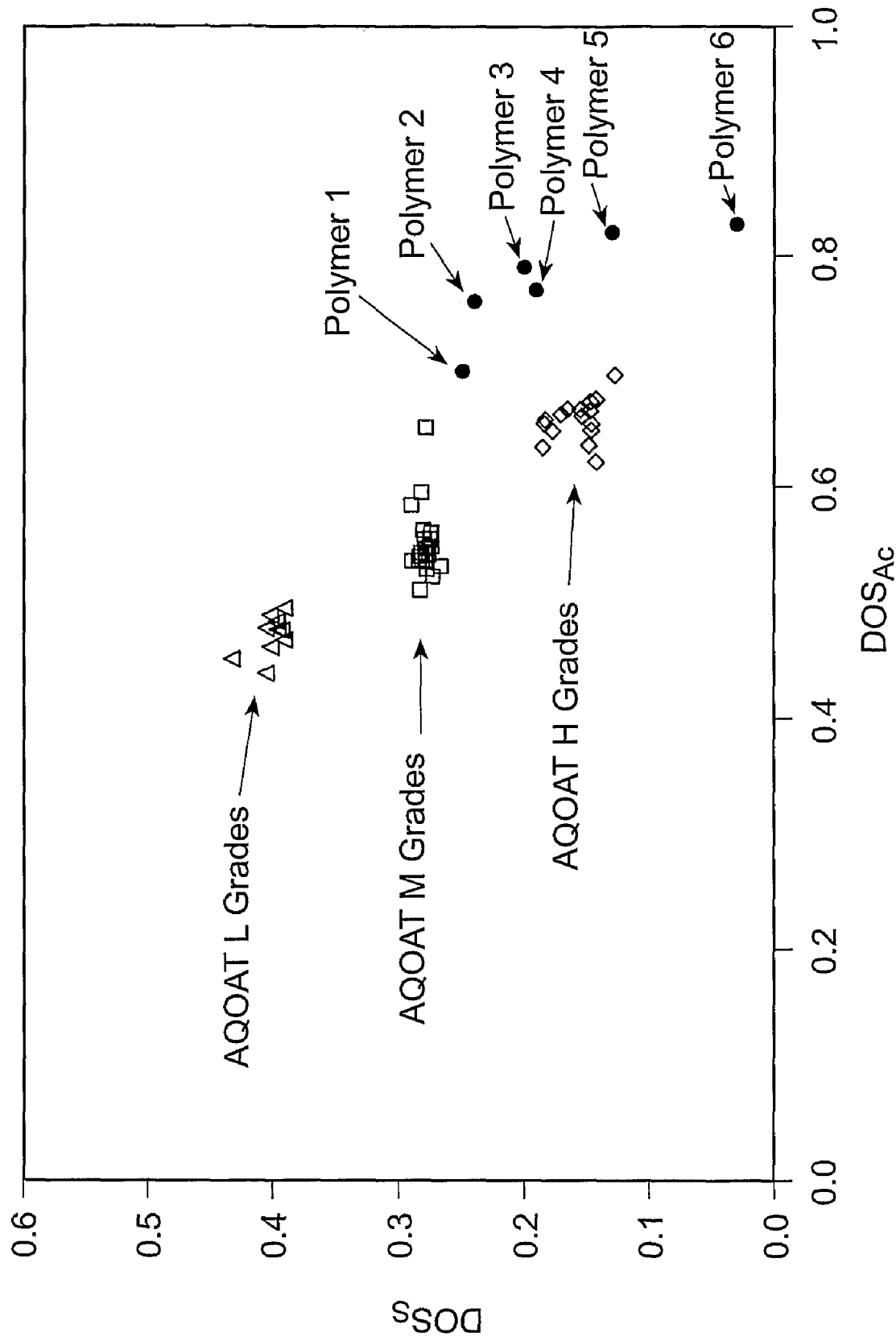

PHARMACEUTICAL COMPOSITIONS WITH ENHANCED PERFORMANCE

The present application claims priority to U.S. provisional application Nos. 60/575,541, filed May 28, 2004 and 60/586,549 filed Jul. 9, 2004, and International application No. PCT/IB2005/001580 filed May 18, 2005, all of which are incorporated by reference herein for all purposes.

FIELD OF THE INVENTION

This invention relates to hydroxypropyl methyl cellulose acetate succinate (HPMCAS) and hydroxypropyl methyl cellulose acetate (HPMCA) polymers with a unique combination of substitution levels, to compositions comprising these polymers and low-solubility drugs that have enhanced aqueous concentrations and/or improved physical stability, to processes for preparing such compositions, and to methods of using such compositions.

BACKGROUND

Pharmaceutical compositions often include polymers to achieve specific desired therapeutic effects, including for use as coating agents, as film-formers, as rate-controlling polymers for sustained or controlled release, as stabilizing agents, as suspending agents, as tablet binders, and as viscosity-increasing agents.

HPMCAS was originally developed as an enteric polymer for pharmaceutical dosage forms and for providing halation-preventing layers on photographic films. See Onda et al., U.S. Pat. No. 4,226,981. Enteric polymers are those that remain intact in the acidic environment of the stomach; dosage forms coated with such polymers protect the drug from inactivation or degradation in the acidic environment or prevent irritation of the stomach by the drug. HPMCAS is currently commercially available from Shin-Etsu Chemical (Tokyo, Japan), known by the trade name "AQOAT." Shin-Etsu manufactures three grades of AQOAT that have different combinations of substituent levels to provide enteric protection at various pH levels. The AS-LF and AS-LG grades (the "F" standing for fine and the "G" standing for granular) provide enteric protection up to a pH of about 5.5. The AS-MF and AS-MG grades provide enteric protection up to a pH of about 6.0, while the AS-HF and AS-HG grades provide enteric protection up to a pH of about 6.8. Shin Etsu gives the following specifications for these three grades of AQOAT polymers:

| Substituent | Composition of Shin Etsu's AQOAT Polymers (wt %) | | |
|---|---|---|---|
| | L Grades | M Grades | H Grades |
| Methoxyl Content | 20.0-24.0 | 21.0-25.0 | 22.0-26.0 |
| Hydroxypropoxyl Content | 5.0-9.0 | 5.0-9.0 | 6.0-10.0 |
| Acetyl Content | 5.0-9.0 | 7.0-11.0 | 10.0-14.0 |
| Succinoyl | 14.0-18.0 | 10.0-14.0 | 4.0-8.0 |

While pharmaceutical formulations of low-solubility drugs and HPMCAS have proven effective, the AQOAT polymers manufactured by Shin Etsu provide only a limited selection of properties for forming such formulations.

What is desired are HPMCAS or HPMCA polymers designed specifically for improving the dissolved drug concentration and the stability of drugs in the composition. Additionally, there is a need to adjust the properties of polymers used in pharmaceutical compositions for numerous applications, including concentration-enhancement and controlled release applications.

SUMMARY OF THE INVENTION

The present invention provides polymers of HPMCAS with a combination of substituent levels that results in improved performance when used in pharmaceutical compositions with a low-solubility drug. In one aspect, the invention provides HPMCAS polymers wherein the degree of substitution of acetyl groups ($DOS_{Ac}$) and the degree of substitution of succinoyl groups ($DOS_S$) on the HPMCAS are selected such that
$DOS_S \geq$ about 0.02,
$DOS_{Ac} \geq$ about 0.65, and
$DOS_{Ac} + DOS_S \geq$ about 0.85.

In another aspect, the invention provides a pharmaceutical composition comprising (a) a low-solubility drug, and (b) an HPMCAS polymer, wherein the degree of substitution of acetyl groups ($DOS_{Ac}$) and the degree of substitution of succinoyl groups ($DOS_S$) on the HPMCAS are selected such that
$DOS_S \geq$ about 0.02,
$DOS_{Ac} \geq$ about 0.65, and
$DOS_{Ac} + DOS_S \geq$ about 0.85.

The invention provides one or more of the following advantages. The HPMCAS polymers have a combination of substituent degree of substitution that enhance the concentration of dissolved drug for low-solubility drugs in a use environment. When used to form solid amorphous dispersions of low-solubility drugs, and in particular, hydrophobic drugs, the polymers allow higher amounts of drug in the dispersion and still remain homogeneous upon storage, while providing enhanced concentrations of dissolved drug in a use environment. When used in combination with drugs that are prone to rapid crystallization from supersaturated aqueous solutions, the polymers of the present invention are particularly effective at sustaining high drug concentrations and thereby enhancing absorption of drug in vivo. Additionally, dispersions of low-solubility drugs and the inventive polymers may provide improved physical stability when compared to dispersions made with commercial grades of HPMCAS. The inventive polymers are also useful in forming blends and mixtures with solubility-improved forms of low-solubility drugs, resulting in concentration enhancements of the same.

The present invention also provides polymers of HPMCA. In one aspect, the invention provides HPMCA polymers wherein the degree of substitution of acetyl groups ($DOS_{Ac}$) on the polymer is at least about 0.15.

In yet another aspect, the invention provides HPMCA polymers wherein the degree of substitution of acetyl groups ($DOS_{Ac}$) on the polymer is about 0.6 or less.

In another aspect, the invention provides HPMCA polymers having a solubility parameter of about 24.0 $(J/cm^3)^{1/2}$ or less.

In still another aspect, the invention provides a pharmaceutical composition comprising (a) a low-solubility drug, and (b) an HPMCA polymer, wherein the degree of substitution of acetyl groups ($DOS_{Ac}$) on the polymer is at least about 0.15.

The HPMCA polymers of the present invention have a novel combination of substituent levels tailored to the specific needs for pharmaceutical compositions, and in particular, for enhancing the concentration of dissolved drug when the compositions is administered to an aqueous use environment. The inventors discovered that when used in combination with drugs that are prone to rapid crystallization from supersaturated aqueous solutions, the polymers are particularly effective at sustaining high drug concentrations and there-by enhancing absorption of drug.

In addition, the added acetyl groups results in the solubility parameter of HPMCA being lower than that of HPMC. As a result, lipophilic drugs have a higher solubility in HPMCA than in HPMC, resulting in solid amorphous dispersions with improved physical stability, and/or higher drug loadings for the same physical stability.

Additionally, adding acetyl groups to HPMC to form HPMCA results in an HPMCA polymer than is more soluble in organic solvents than is HPMC. This provides an advantage when forming solid amorphous dispersions with low-solubility drugs, allowing the use of organic solvents to form the dispersion. It also provides more options when applying coatings to solid dosage forms.

In addition, because HPMCA is non-ionizable and non-acidic, it does not lead to chemical degradation of acid-sensitive drugs or acid-sensitive excipients, unlike ionizable, acidic, or enteric polymers that can rapidly degrade acid-sensitive drugs and excipients under some conditions. All of these properties make HPMCA a desirable polymer for use in pharmaceutical compositions.

The inventors have also discovered that the HPMCA polymers have uses other than enhancing the concentration of low-solubility drugs in aqueous solution. For example, the inventive polymers are useful as coatings or as matrix materials for controlling or delaying the release of drug from a pharmaceutical composition.

The foregoing and other objectives, features, and advantages of the invention will be more readily understood upon consideration of the following detailed description of the invention.

BRIEF DESCRIPTION OF THE DRAWINGS

FIG. 1 shows a plot of the degree of substitution of succinoyl groups ($DOS_S$) versus the degree of substitution of acetyl groups ($DOS_{Ac}$) for three commercial grades of HPMCAS (AQOAT, Shin Etsu, Tokyo, Japan) and the inventive polymers. See Examples for further details of these data.

DETAILED DESCRIPTION OF THE PREFERRED EMBODIMENTS

HPMCA and HPMCAS are substituted cellulosic polymers. By "substituted cellulosic polymer" is meant a cellulose polymer that has been modified by reaction of at least a portion of the hydroxyl groups on the saccharide repeat units with a compound to form an ester-linked or an ether-linked substituent. Cellulose has the following general repeat unit:

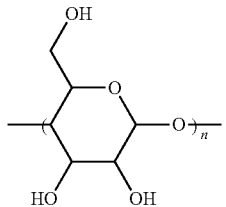

HPMCA and HPMCAS contain 2-hydroxypropoxy groups (—OCH$_2$CH(CH$_3$)OH, hereinafter referred to as hydroxypropoxy groups) ether linked to the saccharide repeat unit by substitution on any hydroxyl group present on the repeat unit, or linked to a hydroxyl group on another hydroxypropoxy group as follows:

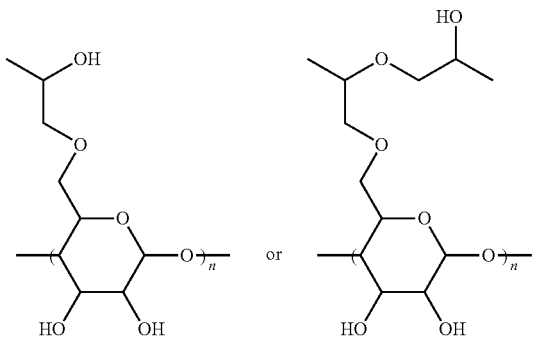

HPMCA and HPMCAS also contain methoxy groups (—OCH$_3$), ether linked to the saccharide repeat unit by substitution on any hydroxyl group present on the repeat unit, as follows:

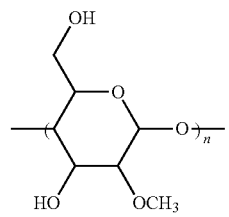

HPMCA and HPMCAS also contain acetyl groups (—COCH$_3$) ester linked to the saccharide repeat unit by substitution on any hydroxyl group present on the repeat unit, as follows:

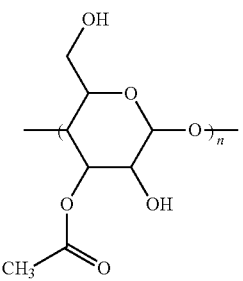

HPMCAS also contains succinoyl groups (—COCH$_2$CH$_2$COOH) ester linked to the saccharide repeat unit by substitution on any hydroxyl group present on the repeat unit, as follows:

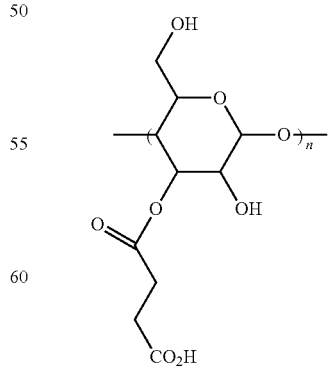

Thus, as used herein and in the claims, by "HPMCAS" is meant a cellulosic polymer comprising 2-hydroxypropoxy groups (—OCH$_2$CH(CH$_3$)OH), methoxy groups (—OCH$_3$), acetyl groups (—COCH$_3$), and succinoyl groups (—COCH$_2$CH$_2$COOH). Other substituents can be included on the polymer in small amounts, provided they do not materially affect the performance and properties of the HPMCAS.

Thus, as used herein and in the claims, by "HPMCA" is meant a cellulosic polymer comprising 2-hydroxypropoxy groups (—OCH$_2$CH(CH$_3$)OH), methoxy groups (—OCH$_3$), and acetyl groups (—COCH$_3$). Other substituents can be included on the polymer in small amounts, provided they do not materially affect the performance and properties of the HPMCA.

The amount of any one substituent on the polymer is characterized by its degree of substitution on the polymer. By "degree of substitution" of a substituent or group on the polymer is meant the average number of that substituent that is substituted on the saccharide repeat unit on the cellulose chain. The substituent may be attached directly to the saccharide repeat unit by substitution for any of the three hydroxyls on the saccharide repeat unit, or they may be attached through a hydroxypropoxy substituent, the hydroxypropoxy substituent being attached to the saccharide repeat unit by substitution for any of the three hydroxyls on the saccharide repeat unit. For example, an acetyl substituent may be attached to a hydroxyl group on the saccharide repeat unit or to the hydroxyl group on a hydroxypropoxy substituent as follows:

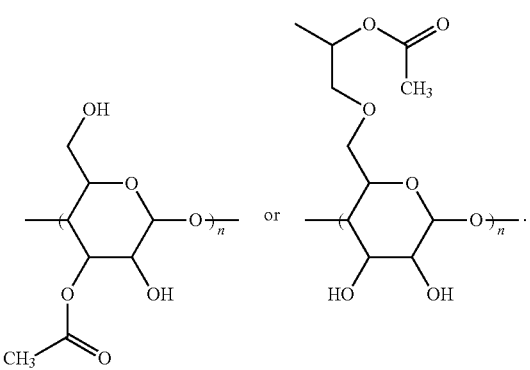

DOS represents the average number of a given substituent on the saccharide repeat unit. Thus, if on average 1.3 hydroxyls on the saccharide repeat unit are substituted with a methoxy group, DOS$_M$ would be 1.3. As another example, if two of the three hydroxyls on the saccharide repeat unit have been substituted with a methoxy group, the DOS$_M$ would be 2.0. In another example, if one of the three hydroxyls on the saccharide repeat unit have been substituted with an hydroxypropoxy group, one of the remaining two hydroxyls on the saccharide repeat unit have been substituted with a methoxy group, and the hydroxyl on the hydroxypropoxy group has been substituted with a methoxy group, the DOS$_{HP}$ would be 1.0 and the DOS$_M$ would be 2.0.

Suitable methods to vary the degree of substitution of various substituents on the polymer, drugs, and methods for forming pharmaceutical compositions, are described in more detail below.

HPMCAS

The prior art HPMCAS polymers supplied by Shin Etsu have the following typical combination of substituent levels (see Comparative Example 1 herein), where the ranges given are for a number of different lots of polymers obtained from Shin Etsu, as indicated in the table:

| Item | Substituent | L Grades Range* | L Grades Average (of 12 lots) | M Grades Range* | M Grades Average (of 28 lots) | H Grades Range* | H Grades Average (of 17 lots) |
|---|---|---|---|---|---|---|---|
| Manufacturer's Certificate of Analysis (wt %) | Methoxyl | 21.7-22.5 | 22.1 ± 0.3 | 22.7-23.6 | 23.1 ± 0.2 | 23.2-24.1 | 23.7 ± 0.3 |
| | Hydroxypropoxyl | 6.8-7.1 | 7.0 ± 0.1 | 7.0-7.9 | 7.3 ± 0.2 | 7.1-7.8 | 7.5 ± 0.2 |
| | Acetyl | 7.2-8.1 | 7.7 ± 0.3 | 8.7-10.8 | 9.3 ± 0.4 | 11.0-12.2 | 11.5 ± 0.3 |
| | Succinoyl | 15.1-16.5 | 15.5 ± 0.4 | 10.8-11.5 | 11.2 ± 0.2 | 5.3-7.6 | 6.5 ± 0.7 |
| Calculated Degree of Substitution** | DOS$_M$ | 1.84-1.91 | 1.87 ± 0.03 | 1.85-1.94 | 1.89 ± 0.02 | 1.84-1.92 | 1.88 ± 0.02 |
| | DOS$_{HP}$ | 0.24-0.25 | 0.25 ± 0.01 | 0.24-0.27 | 0.25 ± 0.01 | 0.23-0.26 | 0.24 ± 0.01 |
| | DOS$_{Ac}$ | 0.44-0.49 | 0.47 ± 0.02 | 0.51-0.65 | 0.55 ± 0.03 | 0.62-0.70 | 0.66 ± 0.02 |
| | DOS$_S$ | 0.39-0.43 | 0.40 ± 0.01 | 0.27-0.29 | 0.28 ± 0.01 | 0.13-0.19 | 0.16 ± 0.02 |
| | DOS$_M$ + DOS$_{Ac}$ + DOS$_S$ | 2.70-2.80 | 2.75 ± 0.03 | 2.65-2.87 | 2.71 ± 0.03 | 2.63-2.73 | 2.70 ± 0.03 |
| | DOS$_{Ac}$ + DOS$_S$ | 0.85-0.89 | 0.88 ± 0.01 | 0.80-0.93 | 0.83 ± 0.03 | 0.77-0.84 | 0.81 ± 0.02 |

*Range of several lots of polymer for each grade (the number of lots is indicated under "Average").
**Degree of substitution calculated as described herein; see Comparative Example 1.

The inventors then found that by varying the combination of substituent levels on the HPMCAS, novel grades of HPMCAS can be prepared in which some low-solubility drugs, particularly those that are hydrophobic, have even higher solubility in the dispersion. This resulted in physically stable solid amorphous dispersions with high drug loadings. Further work with these novel grades of HPMCAS showed dispersions or mixtures with solubility-improved forms of certain drugs provide concentration enhancement and improved inhibition of crystallization or precipitation.

Specifically, the inventors have found that HPMCAS polymers with improved performance and utility have a higher DOS$_{Ac}$, and/or a higher total substitution of acetyl and succinoyl groups (that is, DOS$_{Ac}$+DOS$_S$) than the commercial grades of HPMCAS. Without wishing to be bound by any particular theory or mechanism of action, it is believed that a high DOS$_{Ac}$ is desirable because it provides more hydrophobic groups that lead to an increased solubility of low-solubility drugs in the polymer. At the same time, the degree of substitution of succinoyl groups should have at least a sufficient value so as to render the polymer aqueous soluble or dispersible at a pH of 7 to 8.

The inventors have found that HPMCAS polymers with improved performance and utility for pharmaceutical formulations have a high DOS$_{Ac}$. Thus, in one embodiment, the DOS$_{Ac}$ is at least about 0.65. Preferably, DOS$_{Ac}$ is about 0.70 or more, more preferably about 0.72 or more.

The inventors have also found that HPMCAS polymers with improved performance and utility for pharmaceutical formulations should have a minimum degree of succinoyl groups. Thus, in one embodiment, the $DOS_S$ is at least about 0.02. Preferably, $DOS_S$ is at least about 0.03, and more preferably about 0.05 or more.

In addition, the combined degrees of substitution of acetyl and succinoyl groups on the HPMCAS should be greater than a minimum value. Thus, in one embodiment, $DOS_{Ac}+DOS_S \geq$ about 0.85. Preferably, $DOS_{Ac}+DOS_S \geq$ about 0.88, and more preferably $DOS_{Ac}+DOS_S \geq$ about 0.90. The inventors have found that HPMCAS with this combined degree of substitution of acetyl and succinoyl groups has utility for pharmaceutical formulations.

Turning to the methoxy degree of substitution, the HPMCAS polymers preferably have a $DOS_M$ ranging from about 1.6 to about 2.15. The $DOS_M$ may also be at least about 1.7 or even at least about 1.75. The $DOS_M$ may also be about 2.1 or less, or even 2.0 or less. The inventors have found that HPMCAS with this degree of substitution of methoxy groups has utility for pharmaceutical formulations.

The $DOS_{HP}$ preferably ranges from about 0.10 to about 0.35. The $DOS_{HP}$ may also range from about 0.15 to about 0.30. The inventors have found that HPMCAS with this degree of substitution of hydroxypropoxy groups has utility for pharmaceutical formulations.

The inventors have also found that the combined degrees of substitution of acetyl, succinoyl, and methoxy should be high to obtain high solubilities of low-solubility drugs in the polymer. A high combined degree of substitution by these groups leads to a low degree of substitution of unreacted hydroxyls on the cellulose repeat unit. Unreacted hydroxyls significantly increase the hydrophilic nature of the polymer, and can reduce the solubility of low-solubility drugs in the polymer. Thus, in one embodiment, $DOS_{Ac}+DOS_S+DOS_M \geq$ about 2.7. Preferably, $DOS_{Ac}+DOS_S+DOS_M \geq$ about 2.8, and more preferably $DOS_{Ac}+DOS_S+DOS_M \geq$ about 2.85.

The inventors have discovered that pharmaceutical compositions of drugs made with polymers that meet these criteria provide concentration enhancement or improved physical stability or both relative to control compositions as outlined herein.

The inventors have also discovered that solid amorphous dispersions of hydrophobic drugs and HPMCAS with improved physical stability can be obtained by reducing the difference in solubility parameter between the drug and the polymer. Without wishing to be bound by any particular theory or mechanism of action, it is believed that when the difference in solubility parameter between the HPMCAS and the drug is low, the free energy of mixing of the polymer/drug dispersion is low. The lower the free energy of mixing for the dispersion, the higher the thermodynamic solubility of the drug in the polymer. This means that for a given drug loading in a dispersion, the lower the difference in solubility parameter between the drug and polymer, the more physically stable the dispersion will be (that is, it will either be thermodynamically stable or will have a lower rate of phase separation into a drug-rich phase and a drug-poor phase, as discussed below). Alternatively, a dispersion with a higher drug loading can be formed that has the same physical stability as a dispersion made at a lower drug loading, but with a larger difference in solubility parameter. Methods to calculate the solubility parameter of drugs and HPMCAS based on the degree of substitution are outlined herein.

HPMCA

The inventors discovered that solid amorphous dispersions of some low-solubility drugs, particularly those that are hydrophobic (that is, drugs with solubility parameters of less than about 22 $(J/cm^3)^{1/2}$), with HPMC tend to have poor physical stability due to the mis-match in solubility parameter between the drug and the polymer (the HPMC solubility parameter is greater than about 25 $(J/cm^3)^{1/2}$). The inventors discovered that adding acetyl groups to HPMC to form HPMCA could decrease the solubility parameter of the polymer, resulting in an increased solubility of the drug in the polymer, thereby improving the physical stability of the drugs in dispersions with HPMCA. Upon further research, it was found that HPMCA has beneficial properties that make it suitable for many other pharmaceutical applications.

The degree of substitution of acetyl groups on the HPMCA can vary over a wide range while providing utility for pharmaceutical formulations. Preferably, the $DOS_{Ac}$ is at least about 0.05. HPMCA polymers with a $DOS_{Ac}$ of less than this value have similar properties as HPMC, and therefore, form no part of this invention.

For embodiments when improvement in concentration-enhancement is desired, the HPMCA should be water soluble or dispersible over the physiological pH range of 1-8. Preferably, the HPMCA has an aqueous solubility of at least about 0.1 mg/mL over at least a portion of the pH range of 1 to 8. However, when the value of $DOS_{Ac}$ is too high, the HPMCA becomes so hydrophobic it is no longer water soluble or dispersible.

Thus, in one embodiment, the $DOS_{Ac}$ is equal to or less than about 0.60, preferably equal to or less than about 0.50, and more preferably equal to or less than about 0.45. The inventors have found that HPMCA with $DOS_{Ac}$ values below about 0.6 are water soluble or dispersible.

In another embodiment, the $DOS_{Ac}$ ranges from about 0.15 to about 0.6, preferably from about 0.20 to about 0.50, and more preferably from about 0.25 to about 0.45.

In still another embodiment, the $DOS_{Ac}$ is sufficiently high that the HPMCA polymer has a solubility parameter of about 24.0 $(J/cm^3)^{1/2}$ or less. Preferably, the HPMCA polymer has a solubility parameter of about 23.8 $(J/cm^3)^{1/2}$ or less, and more preferably, about 23.6 $(J/cm^3)^{1/2}$ or less. Methods to estimate the solubility parameter of HPMCA are disclosed herein. When the methoxy degree of substitution ($DOS_M$) is about 1.88 and the hydroxypropoxy degree of substitution ($DOS_{HP}$) is about 0.25, this corresponds to a $DOS_{Ac}$ of greater than about 0.25, preferably greater than about 0.30, and more preferably greater than about 0.35.

For embodiments when the HPMCA is used as a controlled-release matrix material, the $DOS_{Ac}$ should be at least about 0.2. Higher degrees of substitution of acetyl groups may be used to tune the rate of release of drug from the composition. Thus, the $DOS_{Ac}$ may be at least about 0.3, at least about 0.4, at least about 0.5, at least about 0.6, at least about 0.7, at least about 0.8, at least about 0.9, or even at least about 1.0 and still be effective as a controlled-release matrix.

When used as a coating material, the $DOS_{Ac}$ should range from about 0.2 to about 1.0.

The HPMCA polymers also preferably have a $DOS_M$ ranging from about 1.6 to about 2.15. The $DOS_M$ may also be at least about 1.7 or even at least about 1.75. The $DOS_M$ may also be about 2.1 or less, or even 2.0 or less. The inventors have found that HPMCA with this degree of substitution of methoxy groups has utility for pharmaceutical formulations.

The $DOS_{HP}$ preferably ranges from about 0.10 to about 0.35. The $DOS_{HP}$ may also range from about 0.15 to about 0.30. The inventors have found that HPMCA with this degree of substitution of hydroxypropoxy groups has utility for pharmaceutical formulations.

In another embodiment, the total degree of substitution of methoxy and acetyl groups ($DOS_M + DOC_{Ac}$) is at least about 1.9, more preferably at least about 2.0, and most preferably at least about 2.1.

Synthesis of HPMCAS and HPMCA

Methods for synthesis of HPMCAS and HPMCA are well known in the art. See for example Onda et al, U.S. Pat. No. 4,226,981 and *Comprehensive Cellulose Chemistry* by Kelmm et al. (1998; see pages 164-197 and 207-249), the teachings of which are incorporated herein by reference. HPMCA and HPMCAS may be synthesized by treating o-(hydroxypropyl)-o-methylcellulose (i.e., HPMC) with acetic anhydride and acetic anhydride and succinic anhydride, respectively, as set forth herein. Sources for HPMC include Dow (Midland, Mich.), Shin-Etsu (Tokyo, Japan), Ashland Chemical (Columbus, Ohio), Aqualon (Wilmington, Del.), and Colorcon (West Point, Pa.). A variety of HPMC starting materials are available, with various degrees of substitution of hydroxypropoxy and methoxy substituents. One skilled in the art will realize that the choice of HPMC starting material will have an influence on the solubility parameter and other properties of the polymer generated therefrom. In a preferred embodiment, the HPMC has a $DOS_M$ ranging from 1.76 to 2.12, a $DOS_{HP}$ ranging from 0.18 to 0.35, and an apparent viscosity of 2.4 to 3.6 cp. Examples of such polymers include the E3 Prem LV grade available from Dow (Midland, Mich.) and the Pharmacoat Grade 603 type 2910 polymer from Shin Etsu (Japan). Alternatively, the HPMC may be synthesized from cellulose using methods well known in the art. For example, cellulose may be treated with sodium hydroxide to produce swollen alkali cellulose, and then treated with chloromethane and propylene oxide to produce HPMC. See *Comprehensive Cellulose Chemistry* by Kelmm et al. (1998). The HPMC starting material preferably has a molecular weight ranging from about 600 to about 60,000 daltons, preferably about 3,000 to about 50,000 daltons, more preferably about 6,000 to about 30,000 daltons.

Esterification of HPMC is typically carried out by one of two general procedures. In the first procedure, the HPMC is first dispersed or dissolved in a carboxylic acid solvent, such as glacial acetic acid, propionic acid, or butyric acid. The carboxylic acid may be heated to promote dissolution of the HPMC in the solvent. Temperatures ranging from about 50 to about 120° C. may be used, with a temperature of about 85° C. preferred. Preferably the HPMC is dissolved in the solvent; however, the HPMC may only be dispersed in the solvent and formation of the polymer with acceptable properties may still be obtained.

An alkali carboxylate, such as sodium acetate or potassium acetate, is included in the mixture of the carboxylic acid and HPMC. The alkali carboxylate acts as an esterification catalyst. The concentration of alkali carboxylate generally ranges from about 1 to about 20 wt %, preferably about 5 to about 20 wt % of the reaction mixture.

Generally, the concentration of HPMC in the reaction mixture is about 1 to about 50 wt %, preferably about 5 to about 30 wt % of the reaction mixture.

In preparing HPMCA, once the reaction mixture has been prepared, acetic anhydride is added to begin the esterification reaction. The amount of reactant added is determined by the desired degree of esterification desired in the final product.

Once the reaction is complete (generally, about 4 to 24 hours), the HPMCA is precipitated by, for example, addition of a large volume of water saturated with a salt, such as sodium chloride. The precipitated product is then subjected to thorough washing with hot water to remove impurities. Optionally, when the HPMCA is soluble in organic solvents, the precipitated product may be dissolved in an organic solvent, such as acetone or THF, and then re-precipitated and washed, for example, in hot water. The HPMCA product is then thoroughly dried prior to use.

In preparing HPMCAS, once the reaction mixture has been prepared, succinic anhydride and acetic anhydride are added to begin the esterification reaction. The two reactants may be added into the reaction vessel at the same time or consecutively. Alternatively, a portion of one of the reactants may be added to the reaction vessel first followed by a portion of the second reactant; this process may be repeated until all of the desired amount of each reactant has been added. The amount of each reactant added is determined by the desired degree of esterification desired in the final product. Typically, an excess of each reactant is used, usually being 1.0 to 5.0 times the stoichiometric amounts, although excess reactant of 10-times, 50-times, and as much as 100-times the stoichiometric amounts may be used.

Once the reaction is complete (generally, about 4 to 24 hours), a large volume of water is added to the reaction mixture so that the polymer is precipitated. In its protonated form, the polymer is insoluble in water. As long as no base is added, the water remains at low pH and the polymer remains insoluble in the acidic water. The precipitated product is then subjected to thorough washing with water to remove impurities. Optionally, the precipitated product may be dissolved in an organic solvent, such as acetone, and then re-precipitated and washed in water. The product is then thoroughly dried prior to use.

In the second procedure for forming HPMCAS or HPMCA from HPMC, the HPMC is dispersed or dissolved in an organic solvent, such as acetone or dimethylformamide, along with a basic catalyst, such as pyridine or $\alpha$-picoline. The concentration of HPMC in the reaction mixture ranges from about 1 wt % to about 70 wt %, preferably about 5 wt % to about 50 wt %. To form HPMCA, acetic anhydride is then added as described above, and the reaction mixture heated to about 40° C. to about 120° C. for about 2 to about 120 hours to form the HPMCA. To form HPMCAS, the succinic anhydride and acetic anhydride are then added as described above, and the reaction mixture heated to about 40° C. to about 120° C. for about 2 to about 120 hours to form the HPMCAS.

After completion of the esterification reaction, a large volume of 5-15% sulfuric acid or hydrochloric acid is added to the reaction mixture to acidify the mixture, protonate the polymer, and as a result, precipitate the polymer, which is then washed with water thoroughly to remove impurities and dried to form a high purity powdery or granular product.

The resulting polymer generally has a molecular weight that is about 1.7-fold that of the starting HPMC. Thus, the polymer preferably has a molecular weight ranging from about 1,000 to about 100,000 daltons, preferably about 5,000 to about 80,000 daltons, more preferably about 10,000 to about 50,000 daltons. In embodiments where higher molecular weights are desirable, such as when the HPMCA is used as a controlled-release matrix or as a coating material, the HPMCA may have a molecular weight range from about 1,000 to over 1,000,000 daltons.

The degree of substitution of hydroxypropoxy, methoxy, acetyl, and succinoyl groups on the polymer can be determined from the weight percent of the substituent on the polymer, which can be determined using methods well known in the art. See for example, U.S. Pat. No. 4,226,981 and Japanese Pharmaceutical Excipients (1993, pages 182-187), the disclosures of which are herein incorporated by reference.

The weight percentage of substituents is the industrially accepted method for characterization of the amounts of substituents on the polymers. However, the inventors have discovered that the degree of substitution of the substituents on the cellulose backbone provides a more meaningful parameter for determining the effectiveness of a given grade of polymer for use in pharmaceutical compositions. In particular, when the degree of substitution of one component of the polymer is changed, the degrees of substitution of the other components stay the same. However, when weight percent is used, a change in the weight percentage of one component results in a change in the weight percentage of all components of the polymer, even if the degree of substitution is not changed. This is because the weight percent is based on the total weight of the cellulose repeat unit, including all substituents.

By convention, the weight percentage of hydroxypropoxy groups are reported based on the mass of hydroxypropoxy groups (i.e., —OCH$_2$CH(CH$_3$)OH) attached to the saccharide group, the weight percentage of methoxy groups are reported based on the mass of methoxy groups (i.e., —OCH$_3$), the weight percentage of acetyl groups are reported based the mass of acetyl groups (i.e., —COCH$_3$), and the weight percentage of succinoyl groups are reported based on the mass of succinoyl groups (i.e., —COCH$_2$CH$_2$COOH). This convention is used herein when discussing weight percentages of substituents.

Rashan et al. (*Journal of AOAC International*, Vol. 86, No. 4, p. 694-702, 2003) provide a procedure for determining the weight percentage of hydroxypropoxy and methoxy groups on a polymer as follows. A 60-70 mg sample of the polymer is weighted into a vial. To this same vial is added 70-130 mg of adipic acid and a 2-mL portion of 57 wt % hydriodic acid in water. A 2-mL portion of o-xylene is then added into the vial and the vial capped and weighed. The vial is then heated to 150° C. and periodically shaken. After 1 hour of heating, the vial is allowed to cool to ambient temperature and the vial weighed again to assure a weight loss of less than 10 mg. The two phases are allowed to separate, and about 1.5 mL of the top o-xylene layer is removed using a pipet and placed into a small glass vial (without disturbing the bottom aqueous layer). Next, 1-mL of the o-xylene layer that was removed is accurately measured into a 10-mL volumetric flask, diluted to volume with methanol, and mixed well. This is labeled as the Test Sample.

Standard solutions were prepared as follows. Approximately 2 mL o-xylene is placed into a 10-mL volumetric flask. Approximately 200 μL of iodomethane is then added to the flask and the weight of iodomethane added is recorded. Approximately 34 μL of 2-iodopropane is then added to the flask and the weight of iodopropane added is recorded. The contents of the flask are then brought to volume with o-xylene and the flask well mixed.

Next, 80-90 mg adipic acid is added to an 8 mL vial. To this same vial is added 2 mL hydriodic acid (57 wt % in water) and the vial shaken. About 1.5 mL of the top o-xylene layer is removed using a pipet and placed in a small glass vial. Next, 1-mL of the o-xylene layer that was removed is accurately measured into a 10-mL volumetric flask, diluted to volume with methanol, and mixed well. This is labeled as the Standard.

The Test Sample and Standard are analyzed by high-performance liquid chromatography (HPLC) as follows. Mobile Phase A consisted of 90/10 v/v water/methanol and Mobile Phase B consisted of 15/85 v/v water/methanol. A 10-μL volume of the Test Sample or Standard is injected in to an HPLC. The HPLC is equipped with an AQUASIL® column (5 μm, C$_{18}$ 125 Å, 150×4.60 mm). The flow rate is 1.0 mL/min with the following gradient profile: at 0.00 min, 70% Mobile Phase A, 30% Mobile Phase B; at 8.00 min, 40% A, 60% B; at 10.00 min, 15% A, 85% B; at 17 min, 15% A, 85% B; and at 17.01 min, 70% A, 30% B. Detection is by UV at a wavelength of 254 nm.

To calculate the amount of hydroxypropoxy and methoxy on the polymer sample, the standard response factor (RF$_i$) for species i based on the results with the Standard is calculated from the following equation:

$$RF_i = \frac{A_{std,i} * DF_{std,i} * V_{std,i}}{W_{std,i} * PF_i}$$

where $A_{std,i}$ is the peak area obtained for species i, $DF_{std,i}$ is the dilution factor for species i, $V_{std,i}$ is the volume of o-xylene used for preparing the standard, $W_{std,i}$ is the weight, in mg, of species i used for preparing the standard, and $PF_i$ is the purity factor for species i. The response factor is calculated for both iodomethane and for 2-iodopropane.

The amount of species i in the Test Sample is calculated from the following equation:

$$W_i = \frac{A_i * DF_i * V_i}{RF_i}$$

where the variables have the same definitions as above except that the values are for the Test Solution rather than for the Standard. The amount of both iodomethane and 2-iodopropane are calculated in this manner.

The amount (wt %) of methoxy groups (—OCH$_3$) in the polymer is then calculated by the following equation:

$$\text{Methoxy(wt \%)} = 100 \times \frac{31.03}{141.94} \times \frac{W_{iodomethane}}{\text{weight of polymer}}$$

where $W_{iodomethane}$ is given by the above equation.

Similarly, the amount (wt %) of hydroxypropoxy groups (—OCH$_2$CH(CH$_3$)OH) in the polymer is calculated by the following equation:

$$\text{Hydroxypropoxy(wt \%)} = 100 \times \frac{75.09}{169.99} \times \frac{W_{2-iodopropane}}{\text{weight of polymer}}$$

where $W_{2-iodopropane}$ is given by the above equation.

Another procedure for determining the weight percentage of hydroxypropoxy and methoxy groups on a polymer is as set forth in *Japanese Pharmaceutical Excipients*, pages 182-187 (1993).

The weight percentage of acetyl and succinoyl groups in HPMCAS or acetyl groups in HPMCA may be determined by a high-performance liquid chromatography (HPLC) procedure as follows. First, a 12.4-mg sample of the polymer is placed into a glass vial. To the vial, 4 mL of 1.0 N NaOH is added to hydrolyze the polymer by stirring for 4 hours using a magnetic stirrer. Then 4 mL of 1.2 M H$_3$PO$_4$ solution is added to lower the solution pH to less than 3. The sample solution vial is inverted several times to ensure complete mixing. The sample solution is then filtered through a 0.22-μm syringe filter into an HPLC vial prior to analysis.

As a control, a non-hydrolyzed polymer sample is prepared by first weighing out 102.4 mg of the polymer into a vial. To the vial, 4 mL of 20 mM $KH_2PO_4$ solution at pH 7.50 (adjusted for pH by drop wise adding a 1.0 N sodium hydroxide solution) are added to dissolve the polymer by stirring for 2 hours using a magnetic stirrer. Then, 4 mL of 25 mM $H_3PO_4$ solution is added to precipitate the polymer out of solution. The vial is inverted several times to ensure complete mixing. The control solution is then filtered through a 0.22-µm syringe filter into an HPLC vial prior to analysis.

The sample solution and control solution are analyzed by HPLC using a Phenomenex AQUA® 5µ C18 column (without a guard column) with sample detection at 215 nm and a sample size of 10 µL. The mobile phase is 20 mM $KH_2PO_4$ at pH 2.8 at a flow rate of 1.00 mL/min at ambient temperature. A series of standards of acetic acid and succinic acid are prepared for calibration. From the HPLC analysis, the concentration of acetic acid and succinic acid in the sample solution and control solution are determined.

The acetyl and succinoyl contents of the HPMCAS are calculated from the measured acetic and succinic acids in the hydrolyzed sample solution and the measured free acetic and succinic acids in the non-hydrolyzed control solutions. The formulae used for calculations are as follows:

$$\text{Free Acetic Acid(wt \%)} = 100 \times \frac{[\text{Acetic Acid}]_{free}(\text{mg/mL})}{[\text{Polymer}]_{free}(\text{mg/mL})}, \text{ and}$$

$$\text{Free Succinic Acid(wt \%)} = 100 \times \frac{[\text{Succinic Acid}]_{free}(\text{mg/mL})}{[\text{Polymer}]_{free}(\text{mg/mL})},$$

where $[\text{Acetic Acid}]_{free}$ and $[\text{Succinic Acid}]_{free}$ are the concentrations of free acetic and free succinic acids in the non-hydrolyzed control solutions, respectively; and $[\text{Polymer}]_{free}$ is the concentration of the initially added HPMCAS in the non-hydrolyzed control solution. All concentrations are expressed in mg/mL.

The acetyl and succinoyl content of the polymers are determined by the following formulae:

$$\text{Acetyl(wt \%)} = 100 \times \frac{43.04}{60.05} \times \frac{\left([AceticAcid]_{Hyd} - [AceticAcid]_{free} \times \frac{[\text{Polymer}]_{Hyd}}{[\text{Polymer}]_{free}}\right)(\text{mg/mL})}{[\text{Polymer}]_{Hyd}(\text{mg/mL})},$$

and $$\text{Succinoyl(wt \%)} = 100 \times \frac{101.08}{118.09} \times \frac{\left([SuccinicAcid]_{Hyd} - [SuccinicAcid]_{free} \times \frac{[\text{Polymer}]_{Hyd}}{[\text{Polymer}]_{free}}\right)(\text{mg/mL})}{[\text{Polymer}]_{Hyd}(\text{mg/mL})},$$

where $[\text{Acetic Acid}]_{Hyd}$ and $[\text{Succinic Acid}]_{Hyd}$ are the concentrations of acetic and succinic acids in the hydrolyzed sample solution, respectively; $[\text{Acetic Acid}]_{free}$ and $[\text{Succinic Acid}]_{free}$ are the concentrations of free acetic and succinic acids in the non-hydrolyzed control solutions, respectively; and $[\text{Polymer}]_{free}$ and $[\text{Polymer}]_{Hyd}$ are the concentrations of the initially added polymer in the non-hydrolyzed control solution and in the hydrolyzed sample solution, respectively. All concentrations are expressed in mg/mL.

The above analyses give the weight percentages of methoxy, hydroxypropoxy, acetyl, and succinoyl groups on the polymer. This information is used to calculate the degree of substitution for each substituent on the polymer using the following procedure.

First, the weight percentage of the polymer that is the backbone (that is, the fraction of the polymer that is not methoxy, hydroxypropoxy, acetyl, or succinoyl groups) is determined by the following equation:

Backbone(wt %)=100−methoxy(wt %)−hydroxypropoxy(wt %)−acetyl(wt %)−succinoyl(wt %)

Next, the number of moles of backbone per 100 gm of polymer, $M_{backbone}$ is estimated from the following equation:

$$M_{backbone} = \frac{(\text{Backbone(wt \%)} + (\text{methoxy(wt \%)} + \text{hydroxypropoxy(wt \%)}) \times 16)}{159}$$

This equation accounts for the fact that the weight percents for methoxy and hydroxypropoxy groups includes the oxygen that was part of the hydroxyl group on the saccharide repeat unit, while the weight percents for acetyl and succinoyl groups do not. One skilled in the art will realize that this equation is only an approximation; an iterative calculation is required to determine the actual number of moles of backbone per 100 gm of polymer. However, the inventors have found that this approximation generally results in a calculated degree of substitution that is within the error range for measurements of the weight percentages of substituents on the polymer, and greatly reduces the number of calculations required to determine the degree of substitution. As used herein, the degree of substitution is calculated using this approximation.

The degree of substitution of the substituents ($DOS_i$, where i represents the substituent) are then determined by dividing the number of moles of the substituent (calculated by dividing the weight percent of the substituent by the molecular weight of the substituent) by the number of moles of the backbone, as follows:

$$DOS_M = \frac{\text{methoxy(wt \%)}/31.03}{M_{backbone}},$$

$$DOS_{HP} = \frac{\text{hydroxypropoxy(wt \%)}/75.09}{M_{backbone}},$$

$$DOS_{Ac} = \frac{\text{acetyl(wt \%)}/43.04}{M_{backbone}}, \text{ and}$$

$$DOS_S = \frac{\text{succinoyl(wt \%)}/101.8}{M_{backbone}}.$$

Low Solubility Drugs

The term "drug" is conventional, denoting a compound having beneficial prophylactic and/or therapeutic properties when administered to an animal, especially humans. Preferably, the drug is a "low-solubility drug," meaning that the drug has a minimum aqueous solubility at physiologically relevant pH (e.g., pH 1-8) of about 0.5 mg/mL or less. The invention finds greater utility as the aqueous solubility of the drug decreases. Thus, compositions of the present invention are preferred for low-solubility drugs having an aqueous solubility of less than about 0.2 mg/mL, more preferred for low-solubility drugs having an aqueous solubility of less than about 0.1 mg/mL, more preferred for low-solubility drugs having an aqueous solubility of less than about 0.05 mg/mL, and even more preferred for low-solubility drugs having an aqueous solubility of less than about 0.01 mg/mL. In general, it may be said that the drug has a dose-to-aqueous solubility ratio greater than about 10 mL, and more typically greater than about 100 mL, where the aqueous solubility (mg/mL) is the minimum value observed in any physiologically relevant aqueous solution (e.g., those with pH values between 1 and 8) including USP simulated gastric and intestinal buffers, and dose is in mg. Thus, a dose-to-aqueous solubility ratio may be calculated by dividing the dose (in mg) by the aqueous solubility (in mg/mL).

The drug does not need to be a low-solubility drug in order to benefit from this invention, although low-solubility drugs represent a preferred class for use with the invention. Even a drug that nonetheless exhibits appreciable aqueous solubility in the desired environment of use can benefit from the enhanced aqueous concentration and improved bioavailability made possible by this invention if it reduces the size of the dose needed for therapeutic efficacy or increases the rate of drug absorption in cases where a rapid onset of the drug's effectiveness is desired. In such cases, the drug may have an aqueous solubility up to about 1 to 2 mg/mL, or even as high as about 20 to 40 mg/mL.

Preferred classes of drugs include, but are not limited to, antihypertensives, antianxiety agents, anticlotting agents, anticonvulsants, blood glucose-lowering agents, decongestants, antihistamines, antitussives, antineoplastics, beta blockers, anti-inflammatories, antipsychotic agents, cognitive enhancers, cholesterol-reducing agents, triglyceride-reducing agents, anti-atherosclerotic agents, antiobesity agents, autoimmune disorder agents, anti-impotence agents, antibacterial and antifungal agents, hypnotic agents, anti-Parkinsonism agents, anti-Alzheimer's disease agents, antibiotics, anti-depressants, antiviral agents, glycogen phosphorylase inhibitors, and cholesteryl ester transfer protein inhibitors.

Each named drug should be understood to include any pharmaceutically acceptable forms of the drug. By "pharmaceutically acceptable forms" is meant any pharmaceutically acceptable derivative or variation, including stereoisomers, stereoisomer mixtures, enantiomers, solvates, hydrates, isomorphs, polymorphs, pseudomorphs, neutral forms, salt forms and prodrugs. Specific examples of antihypertensives include prazosin, nifedipine, amlodipine besylate, trimazosin and doxazosin; specific examples of a blood glucose-lowering agent are glipizide and chlorpropamide; a specific example of an anti-impotence agent is sildenafil and sildenafil citrate; specific examples of antineoplastics include chlorambucil, lomustine and echinomycin; a specific example of an imidazole-type antineoplastic is tubulazole; a specific example of an anti-hypercholesterolemic is atorvastatin calcium; specific examples of anxiolytics include hydroxyzine hydrochloride and doxepin hydrochloride; specific examples of anti-inflammatory agents include betamethasone, prednisolone, aspirin, piroxicam, valdecoxib, carprofen, celecoxib, flurbiprofen and (+)-N-{4-[3-(4-fluorophenoxy)phenoxy]-2-cyclopenten-1-yl}-N-hyroxyurea; a specific example of a barbiturate is phenobarbital; specific examples of antivirals include acyclovir, nelfinavir, delayerdine, and virazole; specific examples of vitamins/nutritional agents include retinol and vitamin E; specific examples of beta blockers include timolol and nadolol; a specific example of an emetic is apomorphine; specific examples of a diuretic include chlorthalidone and spironolactone; a specific example of an anticoagulant is dicumarol; specific examples of cardiotonics include digoxin and digitoxin; specific examples of androgens include 17-methyltestosterone and testosterone; a specific example of a mineral corticoid is desoxycorticosterone; a specific example of a steroidal hypnotic/anesthetic is alfaxalone; specific examples of anabolic agents include fluoxymesterone and methanstenolone; specific examples of antidepression agents include sulpiride, [3,6-dimethyl-2-(2,4,6-trimethyl-phenoxy)-pyridin-4-yl]-(1-ethylpropyl)-amine, 3,5-dimethyl-4-(3'-pentoxy)-2-(2',4', 6'-trimethylphenoxy)pyridine, pyroxidine, fluoxetine, paroxetine, venlafaxine and sertraline; specific examples of antibiotics include carbenicillin indanylsodium, bacampicillin hydrochloride, troleandomycin, doxycyline hyclate, ampicillin and penicillin G; specific examples of anti-infectives include benzalkonium chloride and chlorhexidine; specific examples of coronary vasodilators include nitroglycerin and mioflazine; a specific example of a hypnotic is etomidate; specific examples of carbonic anhydrase inhibitors include acetazolamide and chlorzolamide; specific examples of antifungals include econazole, terconazole, fluconazole, voriconazole, and griseofulvin; a specific example of an antiprotozoal is metronidazole; specific examples of anthelmintic agents include thiabendazole and oxfendazole and morantel; specific examples of antihistamines include astemizole, levocabastine, cetirizine, levocetirizine, decarboethoxyloratadine and cinnarizine; specific examples of antipsychotics include ziprasidone, olanzepine, thiothixene hydrochloride, fluspirilene, risperidone and penfluridole; specific examples of gastrointestinal agents include loperamide and cisapride; specific examples of serotonin antagonists include ketanserin and mianserin; a specific example of an anesthetic is lidocaine; a specific example of a hypoglycemic agent is acetohexamide; a specific example of an anti-emetic is dimenhydrinate; a specific example of an antibacterial is cotrimoxazole; a specific example of a dopaminergic agent is L-DOPA; specific examples of anti-Alzheimer's Disease agents are THA and donepezil; a specific example of an anti-ulcer agent/H2 antagonist is famotidine; specific examples of sedative/hypnotic agents include chlordiazepoxide and triazolam; a specific example of a vasodilator is alprostadil; a specific example of a platelet inhibitor is prostacyclin; specific examples of ACE inhibitor/antihypertensive agents include enalaprilic acid, quinapril and lisinopril; specific examples of tetracycline antibiotics include oxytetracycline and minocycline; specific examples of macrolide antibiotics include erythromycin, clarithromycin, and spiramycin; a specific example of an azalide antibiotic is azithromycin; specific examples of glycogen phosphorylase inhibitors include [R-(R*S*)]-5-chloro-N-[2-hydroxy-3-{methoxymethylamino}-3-oxo-1-(phenylmethyl)propyl-1H-indole-2-carboxamide and 5-chloro-1H-indole-2-carboxylic acid [(1S)-benzyl-(2R)-hydroxy-3-((3R,4S)-dihydroxy-pyrrolidin-1-yl-)-3-oxypropyl]amide; and specific examples of cholesteryl ester transfer protein (CETP) inhibitors include 2R,4S]-4-[(3,5-bis-trifluoromethyl-benzyl)-methoxycarbonyl-amino]-2-ethyl-6-trifluoromethyl-3, 4-dihydro-2H-quinoline-1-carboxylic acid ethyl ester also known as torcetrapib. Torcetrapib is shown by the following Formula

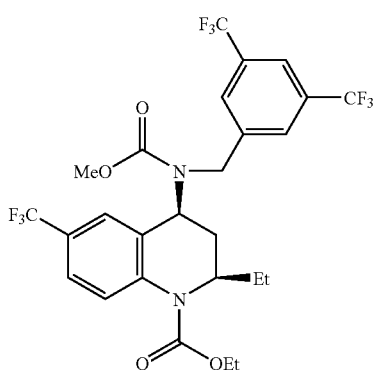

CETP inhibitors, in particular torcetrapib, and methods for preparing such compounds are disclosed in detail in U.S. Pat. Nos. 6,197,786 and 6,313,142, in PCT Application Nos. WO 01/40190A1, WO 02/088085A2, and WO 02/088069A2, the disclosures of which are herein incorporated by reference. Torcetrapib has an unusually low solubility in aqueous environments such as the lumenal fluid of the human GI tract. The aqueous solubility of torcetrapib is less than about 0.04 μg/ml. Torcetrapib must be presented to the GI tract in a solubility-improved form in order to achieve a sufficient drug concentration in the GI tract in order to achieve sufficient absorption into the blood to elicit the desired therapeutic effect. CETP inhibitors are also described in U.S. Pat. No. 6,723,752, which includes a number of CETP inhibitors including (2R)-3-{[3-(4-Chloro-3-ethyl-phenoxy)-phenyl]-[[3-(1,1,2,2-tetrafluoro-ethoxy)-phenyl]-methyl]-amino}-1,1,1-trifluoro-2-propanol. Moreover, CETP inhibitors included herein are also described in U.S. patent application Ser. No. 10/807,838 filed Mar. 23, 2004, and U.S. Patent Application No. 60/612,863, filed Sep. 23, 2004, which includes (2R,4R,4aS)-4-[Amino-(3,5-bis-(trifluoromethyl-phenyl)-methyl]-2-ethyl-6-(trifluoromethyl)-3,4-dihydro-quinoline-1-carboxylic acid isopropyl ester. Further CETP inhibitors include JTT-705, also known as S-[2-([[1-(2-eth-ylbutyl)cyclohexyl]carbonyl]amino)phenyl]2-methylpro-panethioate, and those compounds disclosed in PCT Application No. WO04/020393, such as S-[2-([[1-(2-ethylbutyl)cyclohexyl]carbonyl]amino)phenyl]2-methylpropanethioate, trans-4-[[[2-[[[[3,5-bis(trifluoromethyl)phenyl]methyl](2-methyl-2H-tetrazol-5-yl)amino]methyl]-4-(trifluoromethyl)phenyl]ethylamino]methyl]-cyclohexaneacetic acid and trans-4-[[[2-[[[[3,5-bis(trifluoromethyl)phenyl]methyl](2-methyl-2H-tetrazol-5-yl)amino]methyl]-5-methyl-4-(trifluoromethyl)phenyl]ethylamino]methyl]-cyclohexaneacetic acid, the drugs disclosed in commonly owned U.S. patent application Ser. Nos. 09/918,127 and 10/066,091, the disclosures of both of which are incorporated herein by reference, and the drugs disclosed in the following patents and published applications, the disclosures of all of which are incorporated herein by reference: DE 19741400 A1; DE 19741399 A1; WO 9914215 A1; WO 9914174; DE 19709125 A1; DE 19704244 A1; DE 19704243 A1; EP 818448 A1; WO 9804528 A2; DE 19627431 A1; DE 19627430 A1; DE 19627419 A1; EP 796846 A1; DE 19832159; DE 818197; DE 19741051; WO 9941237 A1; WO 9914204 A1; WO 9835937 A1; JP 11049743; WO 0018721; WO 0018723; WO 0018724; WO 0017164; WO 0017165; WO 0017166; WO 04020393; EP 992496; and EP 987251.

In contrast to conventional wisdom, the relative degree of enhancement in aqueous concentration and bioavailability provided by the compositions of the present invention generally improves for drugs as solubility decreases and hydrophobicity increases. In fact, the inventors have recognized a subclass of hydrophobic drugs that are essentially aqueous insoluble, highly hydrophobic, and are characterized by a set of physical properties. This subclass, referred to herein as "hydrophobic drugs," exhibits dramatic enhancements in aqueous concentration and bioavailability when formulated using the polymers of the present invention. In addition, compositions of hydrophobic drugs and the polymers of the present invention may also have improved physical stability relative to commercial grades of polymer.

The first property of hydrophobic drugs is that they are extremely hydrophobic. By extremely hydrophobic is meant that the Log P value of the drug may have a value of at least 4.0, a value of at least 5.0, and even a value of at least 5.5. Log P, defined as the base 10 logarithm of the ratio of (1) the drug concentration in an octanol phase to (2) the drug concentration in a water phase when the two phases are in equilibrium with each other, is a widely accepted measure of hydrophobicity. Log P may be measured experimentally or calculated using methods known in the art. When using a calculated value for Log P, the highest value calculated using any generally accepted method for calculating Log P is used. Calculated Log P values are often referred to by the calculation method, such as C log P, A log P, and M log P. The Log P may also be estimated using fragmentation methods, such as Crippen's fragmentation method (27 J. Chem. Inf. Comput. Sci. 21 (1987)); Viswanadhan's fragmentation method (29 J. Chem. Inf. Comput. Sci. 163 (1989)); or Broto's fragmentation method (19 Eur. J. Med. Chem.-Chim. Theor. 71 (1984). Preferably the Log P value is calculated by using the average value estimated using Crippen's, Viswanadhan's, and Broto's fragmentation methods.

The second property of hydrophobic drugs is that they have a low solubility parameter, as calculated using the methods described herein. The solubility parameter may be about 22 $(J/cm^3)^{1/2}$ or less, about 21.5 $(J/cm^3)^{1/2}$ or less, and even about 21 $(J/cm^3)^{1/2}$ or less.

Primarily as a consequence of these properties, hydrophobic drugs typically have an extremely low aqueous solubility. By extremely low aqueous solubility is meant that the minimum aqueous solubility at physiologically relevant pH (pH of 1 to 8) is less than about 100 μg/ml and often less than about 10 μg/ml. In addition, hydrophobic drugs often have a very high dose-to-solubility ratio. Extremely low aqueous solubility often leads to poor or slow absorption of the drug from the fluid of the gastrointestinal tract, when the drug is dosed orally in a conventional manner. For extremely low solubility drugs, poor absorption generally becomes progressively more difficult as the dose (mass of drug given orally) increases. Thus, a second property of hydrophobic drugs is a very high dose (in mg) to solubility (in mg/ml) ratio (ml). By "very high dose-to-solubility ratio" is meant that the dose-to-solubility ratio may have a value of at least 1000 ml, at least 5,000 ml, or even at least 10,000 ml.

Hydrophobic drugs also typically have very low absolute bioavailabilities. Specifically, the absolute bioavailability of drugs in this subclass when dosed orally in their unformulated state (i.e., drug alone) is less than about 10% and more often less than about 5%.

One class of hydrophobic drugs that work well in compositions comprising the polymers of the present invention is CETP inhibitors. Solid amorphous dispersions of CETP inhibitors and the polymers of the present invention show dramatic improvements in bioavailability and concentration-enhancement in both in vitro and in vivo tests relative to crystalline drug alone.

The inventors have also found that compositions comprising the polymers of the present invention and CETP inhibitors may be used in combination with 3-hydroxy-3-methylglutaryl-coenzyme A reductase (HMG-CoA reductase) inhibitors. In one embodiment, a unitary dosage form comprises (1) a solid amorphous dispersion comprising a CETP inhibitor and a polymer of the present invention and (2) an HMG-CoA reductase inhibitor. In one aspect, the HMG-CoA reductase inhibitor is from a class of therapeutics commonly called statins. Preferably the HMG-CoA reductase inhibitor is selected from the group consisting of fluvastatin, lovastatin, pravastatin, atorvastatin, simvastatin, cerivastatin, rivastatin, mevastatin, velostatin, compactin, dalvastatin, fluindostatin, rosuvastatin, pitivastatin, dihydrocompactin, and pharmaceutically acceptable forms thereof. By "pharmaceutically acceptable forms" is meant any pharmaceutically acceptable derivative or variation, including stereoisomers, stereoisomer mixtures, enantiomers, solvates, hydrates, isomorphs, polymorphs, salt forms and prodrugs. In a more preferred embodiment, the HMG-CoA reductase inhibitor is selected from the group consisting of atorvastatin, the cyclized lactone form of atorvastatin, a 2-hydroxy, 3-hydroxy or 4-hydroxy derivative of such compounds, and pharmaceutically acceptable forms thereof. Even more preferably, the HMG-CoA reductase inhibitor is atorvastatin hemicalcium trihydrate. Further details of such dosage forms are provided in commonly owned, pending U.S. patent application Ser. No. 10/739,750, filed Dec. 18, 2003, the disclosures of which are incorporated herein.

Acid-Sensitive Drugs

In one embodiment of the invention, the drug is an acid-sensitive drug, meaning that the drug either chemically reacts with or otherwise degrades in the presence of acidic species. Acid-sensitive drugs often include functional groups that are reactive under acidic conditions, such as sulfonyl ureas, hydroxamic acids, hydroxy amides, carbamates, acetals, hydroxy ureas, esters, and amides. Drugs that include such functional groups may be prone to reactions such as hydrolysis, lactonization, or transesterification in the presence of acidic species.

Acid-sensitive drugs may be identified experimentally as follows. A sample of the drug is administered to an acidic aqueous solution and a plot is made of drug concentration versus time. The acidic solution should have a pH of from 1-4. Drugs that are acid sensitive are those for which the drug concentration decreases by at least 1% within 24 hours of administration of the drug to the acidic solution. If the drug concentration changes by 1% in the 6-24 hour time period, then the drug is "slightly acid-sensitive." If the drug concentration changes by 1% in the 1-6 hour time period, then the drug is "moderately acid-sensitive." If the drug concentration changes by 1% in less than 1 hour, then the drug is "highly acid-sensitive." The present invention finds increasing utility for drugs that are slightly acid-sensitive, moderately acid-sensitive and highly acid-sensitive.

Specific examples of acid-sensitive drugs are set forth below, by way of example only. Each named drug should be understood to include the neutral form of the drug, pharmaceutically acceptable salts, and prodrugs. Examples of acid-sensitive drugs include quinoxaline-2-carboxylic acid [4(R)-carbamoyl-1(S)-3-fluorobenzyl-2(S),7-dihydroxy-7-methyl-octyl]amide; quinoxaline-2-carboxylic acid [1-benzyl-4-(4,4-difluoro-cyclohexyl)-2-hydroxy-4-hydroxycarbamoyl-butyl]-amide; quinoxaline-2-carboxylic acid [1-benzyl-4-(4,4-difluoro-1-hydroxy-cyclohexyl)-2-hydroxy-4-hydroxycarbamoyl-butyl]-amide; (+)-N-{3-[3-(4-fluorophenoxy)phenyl]-2-cyclopenten-1-yl}-N-hydroxyurea; omeprazole; etoposide; famotidine; erythromycin; quinapril; lansoprazole; and progabide.

HPMCA has particular utility in compositions with acid sensitive drugs because the polymer is not acidic and is neutral. As a result, compositions comprising acid sensitive drugs and HPMCA have improved chemical stability relative to compositions comprising acid sensitive drugs and acidic polymers, such as HPMCAS.

Solubility Parameters

Solubility parameters are a well-known tool in the art used to correlate and predict cohesive and adhesive properties of materials. A complete discussion of solubility parameters is provided in Barton's *Handbook of Solubility Parameters and Other Cohesion Parameters* (CRC Press, 1983, hereinafter referred to as "Barton"), which is hereby incorporated by reference.

While several methods can be used to determine the solubility parameter of a given compound, in this specification and in the claims, by "solubility parameter" is meant the Hildebrand solubility parameter calculated from group molar cohesive energy constants, as described herein and in Barton, pages 61 to 66. Hildebrand solubility parameters have units of $(J/cm^3)^{1/2}$. Specifically, the solubility parameter for compound i, $\delta_i$, is calculated from $$\delta_i = \left[\frac{-\sum_z U_z}{\sum_z V_z}\right]^{1/2}, \quad (V)$$

where z represents a contributing group on compound i, $U_z$ is the molar vaporization energy (at 25° C.) of the contributing group, and $V_z$ is the molar volume (at 25° C.) of the contributing group. The following table gives group contributions to the molar vaporization energy and molar volume for various groups. Thus, knowing the chemical structure of a compound, the solubility parameter of the compound can be calculated using Equation V and the group contributions given in the following table.

| Group Contributions to the Molar Vaporization Energy and Molar Volume at 25° C. | | |
|---|---|---|
| GROUP, Z | $-U_z$ (kJ/mol) | $V_z$ (cm$^3$ mol) |
| —CH$_3$ | 4.71 | 33.5 |
| —CH$_2$— | 4.94 | 16.1 |
| \CH— / | 3.43 | −1.0 |
| \/ CH /\ | 1.47 | −19.2 |
| H$_2$C= | 4.31 | 28.5 |
| —CH= | 4.31 | 13.5 |

Group Contributions to the Molar Vaporization Energy and Molar Volume at 25° C.

| GROUP, Z | $-U_z$ (kJ/mol) | $V_z$ (cm³/mol) |
|---|---|---|
| $\diagup\mathrm{C}\!\!=\!\!\diagdown$ | 4.31 | −5.5 |
| HC≡ | 3.85 | 27.4 |
| —C≡ | 7.07 | 6.5 |
| Phenyl | 31.9 | 71.4 |
| Phenylene (o, m, p) | 31.9 | 52.4 |
| Phenyl (trisubstituted) | 31.9 | 33.4 |
| Phenyl (tetrasubstituted) | 31.9 | 14.4 |
| Phenyl (pentasubstituted) | 31.9 | −4.6 |
| Phenyl (hexasubstituted) | 31.9 | −23.6 |
| Ring closure, 5 or more atoms | 1.05 | 16 |
| Ring closure, 3 or 4 atoms | 3.14 | 18 |
| Conjugation in ring, each double bond | 1.67 | −2.2 |
| Halogen attached to C atom with double bond | -20% of halogen $U_z$ | |
| —F | 4.19 | 18.0 |
| —F (disubstituted) | 3.56 | 20.0 |
| —F (trisubstituted) | 2.30 | 22.0 |
| —CF$_2$ | 3.28 | 23.1 |
| —CF$_2$ (for perfluoro compounds) | 4.27 | 23.0 |
| —CF$_3$ | 8.09 | 54.8 |
| —CF$_3$ (for perfluoro compounds) | 4.27 | 57.5 |
| —Cl | 11.55 | 24.0 |
| —Cl (disubstituted) | 9.63 | 26.0 |
| —Cl (trisubstituted) | 7.53 | 27.3 |
| —Br | 15.49 | 30.0 |
| —Br (disubstituted) | 12.4 | 31.0 |
| —Br (trisubstituted) | 10.7 | 32.4 |
| —I | 19.05 | 31.5 |
| —I (disubstituted) | 16.7 | 33.5 |
| —I (trisubstituted) | 16.3 | 37.0 |
| —CN | 25.5 | 24.0 |
| —OH | 29.8 | 10.0 |
| —OH (disubstituted or on adjacent C atoms) | 21.9 | 13.0 |
| —O— | 3.35 | 3.8 |
| —CHO (aldehyde) | 21.4 | 22.3 |
| —CO— | 17.4 | 10.8 |
| —CO$_2$— | 18.0 | 18.0 |
| —CO$_3$— (carbonate) | 17.6 | 22.0 |
| —C$_2$O$_3$— (anhydride) | 30.6 | 30.0 |
| HCOO— (formate) | 18.0 | 32.5 |
| —CO$_2$CO$_2$— (oxalate) | 26.8 | 37.3 |
| —HCO$_3$ | 12.6 | 18.0 |
| —COF | 13.4 | 29.0 |
| —COCl | 17.6 | 38.1 |
| COBr | 24.2 | 41.6 |
| COI | 29.3 | 48.7 |
| —NH$_2$ | 12.6 | 19.2 |
| —NH— | 8.4 | 4.5 |
| $\diagdown\mathrm{N}\!\!-$ | 4.2 | −9.0 |
| —N= | 11.7 | 5.0 |
| —NHNH$_2$ | 22.0 | — |
| —NNH$_2$ | 16.7 | 16 |
| —NHNH | 16.7 | 16 |
| —N$_2$ (diazo) | 8.4 | 23 |
| —N=N— | 4.2 | — |
| $\diagdown\mathrm{C}\!\!=\!\!\mathrm{N}\!\!-\!\!\mathrm{N}\!\!=\!\!\mathrm{C}\diagup$ | 20.1 | 0 |
| —N=C=N— | 11.47 | — |
| —NC | 18.8 | 23.1 |
| —NF$_2$ | 7.66 | 33.1 |
| —NF— | 5.07 | 24.5 |
| —CONH$_2$ | 41.9 | 17.5 |
| —CONH— | 33.5 | 9.5 |
| —CON$\diagdown\diagup$ | 29.5 | −7.7 |
| HCON$\diagdown\diagup$ | 27.6 | 11.3 |
| HCONH— | 44.0 | 27.0 |
| —NHCOO— | 26.4 | 18.5 |
| —NHCONH— | 50.2 | — |
| —NHCON$\diagdown\diagup$ | 41.9 | — |
| $\diagdown\mathrm{NCON}\diagup$ | 20.9 | −14.5 |
| NH$_2$COO— | 37.0 | — |
| —NCO | 28.5 | 35.0 |
| —ONH$_2$ | 19.1 | 20.0 |
| $\diagdown\mathrm{C}\!\!=\!\!\mathrm{NOH}$ | 25.1 | 11.3 |
| —CH=NOH | 25.1 | 24.0 |
| —NO$_2$ (aliphatic) | 29.3 | 24.0 |
| —NO$_2$ (aromatic) | 15.36 | 32.0 |
| —NO$_3$ | 20.9 | 33.5 |
| —NO$_2$ (nitrite) | 11.7 | 33.5 |
| —NHNO$_2$ | 39.8 | 28.7 |
| —NNO | 27.2 | 10 |
| —SH | 14.44 | 28.0 |
| —S— | 14.15 | 12 |
| —S$_2$— | 23.9 | 23.0 |
| —S$_3$— | 13.40 | 47.2 |
| $\diagdown\mathrm{SO}\diagup$ | 39.1 | — |
| SO$_3$ | 18.8 | 27.6 |
| SO$_4$ | 28.5 | 31.6 |
| —SO$_2$Cl | 37.1 | 43.5 |
| —SCN | 20.1 | 37.0 |
| —NCS | 25.1 | 40.0 |
| P | 9.42 | −1.0 |
| PO$_3$ | 14.2 | 22.7 |
| PO$_4$ | 20.9 | 28.0 |
| PO$_3$(OH) | 31.8 | 32.2 |
| Si | 3.4 | 0 |
| SiO$_4$ | 21.8 | 20.0 |
| B | 13.8 | −2.0 |
| BO$_3$ | 0.0 | 20.4 |
| Al | 13.8 | −2.0 |
| Ga | 13.8 | −2.0 |
| In | 13.8 | −2.0 |
| Tl | 13.8 | −2.0 |
| Ge | 8.1 | −1.5 |
| Sn | 11.3 | 1.5 |
| Pb | 17.2 | 2.5 |
| As | 13.0 | 7.0 |
| Sb | 16.3 | 8.9 |

For example, the CETP inhibitor [2R,4S]-4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester, also known as torcetrapib, has the chemical structure previously shown. The group contributions for torcetrapib may be obtained from the above tables and are summarized in the following table:

| Group, z | Number of Groups | $-U_z$ (kJ/mol) | $V_z$ (cm$^3$/mol) | $\Sigma -U_z$ (kJ/mol) | $\Sigma V_z$ (cm$^3$/mol) |
| --- | --- | --- | --- | --- | --- |
| CH$_3$ | 3 | 4.71 | 33.5 | 14.1 | 100.5 |
| CH$_2$ | 4 | 4.94 | 16.1 | 19.8 | 64.4 |
| >CH— | 2 | 3.43 | −1 | 6.9 | −2 |
| Phenyl (trisubstituted) | 2 | 31.9 | 33.4 | 63.8 | 66.8 |
| Ring closure (5 or more atoms) | 1 | 1.05 | 16 | 1.1 | 16 |
| —O— | 2 | 3.35 | 3.8 | 6.7 | 7.6 |
| —CO— | 2 | 17.4 | 10.8 | 34.8 | 21.6 |
| >N— | 2 | 4.2 | −9 | 8.4 | −18 |
| —CF$_3$ | 3 | 8.09 | 54.8 | 24.3 | 164.4 |
| Total | | | | 179.8 | 421.3 |

These values can then be inserted into equation V, as follows:

$$\delta_{torcetrapib} = \left[ \frac{-\sum_z U_z}{\sum_z V_z} \right]^{1/2}$$

$$= \left[ \frac{179.8 \text{ kJ/mol} * 1000 \text{ J/kJ}}{421.3 \text{ (cm}^3\text{/mol)}} \right]^{1/2}$$

$$= 20.66 \text{ (J/cm}^3\text{)}^{1/2}$$

The same procedure can be used to calculate the solubility parameter of a polymer. For polymers, the average number of groups on each repeat unit are calculated, and the values of the group contributions are used to calculate the solubility parameter. For example, HPMCAS has the following general structure

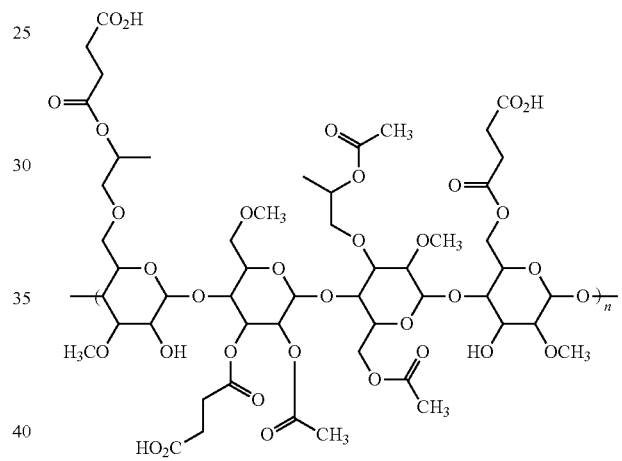

The "medium" grade of HPMCAS (AQOAT-M) can be obtained from Shin-Etsu (Japan) having the following substitution: 7.3 wt % hydroxypropoxy, 23.1 wt % methoxy, 9.3 wt % acetyl, and 11.2 wt % succinoyl. Based on this combination of substituent levels and using the procedure described above, the degrees of substitution of the various substituents are as follows: 0.25 hydroxypropoxy, 1.89 methoxy, 0.55 acetyl, and 0.28 succinoyl. Using this degree of substitution and the structure of the cellulose backbone, the solubility parameter of HPMCAS-M is calculated as follows

| Group, z | Number of Groups | $-U_z$ (kJ/mol) | $V_z$ (cm$^3$/mol) | $\Sigma -U_z$ (kJ/mol) | $\Sigma V_z$ (cm$^3$/mol) |
| --- | --- | --- | --- | --- | --- |
| —CH$_3$ | 2.72 | 4.71 | 33.5 | 12.8 | 91.1 |
| —CH$_2$— | 1.81 | 4.94 | 16.1 | 8.9 | 29.1 |
| >CH— | 5.25 | 3.43 | −1 | 18 | −5.2 |
| Ring closure (5 or more atoms) | 1.00 | 1.05 | 16 | 1.1 | 16 |
| —OH | 0.25 | 30 | 10 | 7.5 | 2.5 |
| —O— | 4.17 | 3.35 | 3.8 | 14 | 15.8 |
| —COO— | 0.83 | 18 | 18 | 14.9 | 14.9 |
| COOH | 0.28 | 27.6 | 28.5 | 7.7 | 8 |
| Total | | | | 84.9 | 172.2 |

These values can then be inserted into equation V, as follows:

$$\delta_{AQOAT-M} = \left[\frac{-\sum_z U_z}{\sum_z V_z}\right]^{1/2}$$

$$= \left[\frac{84.9 \text{ kJ/mol} * 1000 \text{ J/kJ}}{172.2 \text{ (cm}^3\text{/mol)}}\right]^{1/2}$$

$$= 22.20 \text{ (J/cm}^3\text{)}^{1/2}$$

Using this procedure, the solubility parameter of the various grades of commercially available HPMCAS can be calculated. Using the average degree of substitution for the three grades of AQOAT polymers from Shin Etsu, the solubility parameters are as follows (see Comparative Example 1). These data show that small changes in the solubility parameter can lead to significant changes in the polymer properties. For example, as shown in Example 3 herein, the solubility of the drug torcetrapib in the M grade of HPMCAS is 25 to 30 wt %, while the solubility of torcetrapib in the H grade is 35-40 wt %. This substantial increase in solubility results with only a 0.21 increase in solubility parameter for the polymer.

| Polymer Grade | Solubility Parameter $(J/cm^3)^{1/2}$ |
| --- | --- |
| AQOAT-L Grades | 22.75 |
| AQOAT-M Grades | 22.20 |
| AQOAT-H Grades | 21.99 |

As previously stated, the HPMCAS polymers of the present invention have a higher $DOS_{Ac}$, and/or a higher total substitution of acetyl and succinoyl groups (that is, $DOS_{Ac}+DOS_s$) than the commercial grades of HPMCAS. This combination of substituent levels generally results in a lower solubility parameter for the inventive polymers than for the commercial grades. Thus, in one embodiment, the HPMCAS polymers of the present invention have a solubility parameter of less than 21.99, preferably less than about 21.90, more preferably less than about 21.80, and even more preferably less than about 21.75.

Pharmaceutical Compositions

In one embodiment, the present invention provides a pharmaceutical composition comprising a low-solubility drug and a polymer of the present invention. The amount of the polymer relative to the amount of drug present in the compositions of the present invention depends on the drug and combination of substituent levels on the polymer and may vary widely from a drug-to-polymer weight ratio of from 0.01 to about 100 (e.g., 1 wt % drug to 99 wt % drug). In most cases it is preferred that the drug-to-polymer ratio is greater than about 0.05 (4.8 wt % drug) and less than about 20 (95 wt % drug).

In a preferred embodiment, the composition has a high loading of drug. By "high loading of drug" is meant that the pharmaceutical composition comprises at least about 40 wt % drug. Preferably, the pharmaceutical composition comprises at least about 45 wt % drug, and more preferably at least about 50 wt % drug. Such high loadings of drug are desirable to keep the mass of the pharmaceutical composition at a low value.

The low-solubility drug and the polymer may be combined in any manner. In one embodiment, the composition comprises a combination of a low-solubility drug and the polymer. "Combination" as used herein means that the low-solubility drug and the polymer may be in physical contact with each other or in close proximity but without the necessity of being physically mixed. For example, the composition may be in the form of a multi-layer tablet, as known in the art, wherein one or more layers comprises a low-solubility drug and one or more different layers comprises the polymer. Yet another example may constitute a coated tablet wherein either the low-solubility drug or the polymer or both may be present in the tablet core and the coating may comprise a low-solubility drug or the polymer or both. Alternatively, the combination can be in the form of a simple dry physical mixture wherein both the low-solubility drug and the polymer are mixed in particulate form and wherein the particles of each, regardless of size, retain the same individual physical properties that they exhibit in bulk.

Combinations of low-solubility drugs and a polymer may be formed in any conventional way such as by blending the dry ingredients including the low-solubility drug, the polymer, and any other excipients appropriate to forming the desired dosage form using V-blenders, planetary mixers, vortex blenders, mills, extruders such as twin-screen extruders, and trituration processes. The ingredients can be combined in granulation processes utilizing mechanical energy, such as ball mills or roller compactors. They may also be combined using wet granulation methods in high-shear granulators or fluid bed granulators wherein a solvent or wetting agent is added to the ingredients or the polymer may be dissolved in a solvent and used as a granulating fluid. The polymer may be added as a coating to tablets preformed by a compression process from a mixture containing a low-solubility drug, the coating taking place in a spray-coating process using, for example, a pan coater or a fluidized-bed coater.

Alternatively, the compositions of the present invention may be co-administered, meaning that the low-solubility drug can be administered separately from, but within the same general time frame as, the polymer. Thus, the low-solubility drug can, for example, be administered in its own dosage form that is taken at approximately the same time as the polymer that is in a separate dosage form. If administered separately, it is generally preferred to administer both the low-solubility drug and the polymer within 60 minutes of each other, so that the two are present together in the environment of use. When not administered simultaneously, the polymer is preferably administered prior to the low-solubility drug.

In one embodiment, the low-solubility drug is intimately mixed with the polymer of the present invention. As used herein, by "intimately mixed" or "intimate mixture" is meant that the low-solubility drug and polymer are in physical contact with each other or in close proximity to each other in the composition. For example, the low-solubility drug and the polymer may be dry or wet granulated using the methods noted above. Alternatively, the low-solubility drug and the polymer may be in the form of a solid amorphous dispersion, as described herein below. Alternatively, the low-solubility drug may be in the form of particles at least partially coated with the polymer. By "particles" is meant individual crystals of the drug when the drug is crystalline. When the drug is amorphous, "particles" refers to individual particles comprising drug in amorphous form. In general, the particles may range in size from about 0.1 μm to about 500 μm. By "at least partially coated" with the polymer means that the polymer partially coats at least a portion of the surface of the drug particles. The polymer may coat only a portion of the drug particle, or may fully coat or encapsulate the entire surface of the drug particle. Intimate mixtures of the low-solubility drug and the polymer are preferred because when the composition is administered to an aqueous use environment the drug and polymer can begin to dissolve together in close proximity, resulting in concentration enhancement and/or an improvement in bioavailability. This is in contrast to an enteric coated tablet consisting, for example, of a drug-containing core coated with an enteric polymer, where the polymer may dissolve first in the use environment, followed by dissolution of the drug from the core. In such controlled release devices the polymer and drug may not dissolve together in close proximity and no enhancement in concentration or bioavailability may be obtained.

In a preferred embodiment, the composition comprises a combination of a low-solubility drug and the polymer, wherein the low-solubility drug is in a solubility-improved form. By "solubility-improved form" is meant a form of the drug that is capable of supersaturating, at least temporarily, an aqueous use environment by a factor of about 1.1-fold or more, preferably about 1.25-fold or more, more preferably about 2.0-fold or more, relative to the solubility of the crystalline form of the low-solubility drug. That is, the solubility-improved form provides a maximum dissolved drug concentration of the low-solubility drug that is at least about 1.1-fold, more preferably at least about 1.25-fold, even more preferably at least about 2.0-fold the equilibrium drug concentration provided by the crystalline form of the low-solubility drug alone (or the amorphous form if the crystalline form is unknown). Alternatively, the solubility-improved form provides an area under the drug concentration versus time curve (AUC) in the use environment that is at least about 1.1-fold, preferably at least 1.25-fold and more preferably at least 2.0-fold that provided by the control composition. The control composition is the lowest-energy or most stable crystalline form of the low-solubility drug alone, which is the low-solubility drug in bulk crystalline form, or the amorphous form if the crystalline form is unknown. It is to be understood that the control composition is free from solubilizers or other components that would materially affect the solubility of the low-solubility drug, and that the low-solubility drug is in solid form in the control composition.

The solubility-improved form may comprise a solid amorphous dispersion of the low-solubility drug in a concentration-enhancing polymer or low molecular weight water-soluble material, as described in detail below. The solubility-improved form may also comprise a crystalline highly soluble form of the low-solubility drug such as a salt; a high-energy crystalline form of the low-solubility drug; a hydrate or solvate crystalline form of a low-solubility drug; an amorphous form of a low-solubility drug (for a low-solubility drug that may exist as either amorphous or crystalline); a mixture of the low-solubility drug (amorphous or crystalline) and a solubilizing agent; or a solution of the low-solubility drug dissolved in an aqueous or organic liquid. Such solubility-improved forms are disclosed in commonly assigned U.S. patent application Ser. No. 09/742,785, filed Dec. 20, 2000, the disclosure of which is incorporated herein by reference. The solubility-improved form may also comprise a solid adsorbate comprising a low-solubility drug adsorbed onto a substrate, the substrate having a surface area of at least 20 m$^2$/g, and wherein at least a major portion of the low-solubility drug in the solid adsorbate is amorphous. Such solid adsorbates are disclosed in commonly assigned copending U.S. patent application Ser. No. 10/173,987, filed Jun. 17, 2002, which is incorporated in its entirety by reference. The solubility-improved form may also comprise a low-solubility drug formulated in a self-emulsifying lipid vehicle of the type disclosed in commonly assigned copending U.S. patent application Ser. No. 10/175,643 filed on Jun. 19, 2002, which is also incorporated in its entirety by reference.

Solid Amorphous Dispersions

In another embodiment, a low-solubility drug and the polymer are combined and formed into a solid amorphous dispersion. By "solid amorphous dispersion" is meant a solid material in which at least a portion of the low-solubility drug is in the amorphous form and dispersed in the polymer. Solid amorphous dispersions are preferred because such solid amorphous dispersions are often capable of achieving high concentrations of dissolved drug in in vitro and in vivo use environments.

"Amorphous" refers to material that does not have long-range three-dimensional translational order, and is intended to include not only material which has essentially no order, but also material which may have some small degree of order, but the order is in less than three dimensions and/or is only over short distances. Partially crystalline materials and crystalline mesophases with, e.g., one- or two-dimensional translational order (liquid crystals), or orientational disorder (orientationally disordered crystals), or with conformational disorder (conformationally disordered crystals) are intended to be included within the term "amorphous" as well.

Preferably, at least a major portion of the drug in the solid amorphous dispersion is amorphous. As used herein, the term "a major portion" of the drug means that at least about 60% of the drug in the dispersion is in the amorphous form, rather than the crystalline form. It has been found that the aqueous concentration of the drug in a use environment tends to improve as the fraction of drug present in the amorphous state in the dispersion increases. Accordingly, a "major portion" of the drug in the dispersion is amorphous and preferably the drug in the dispersion is substantially amorphous. As used herein, a "major portion" and "substantially amorphous" mean that the amount of the drug in crystalline form does not exceed about 40 wt % and about 25 wt %, respectively. More preferably, the drug in the dispersion is "almost completely amorphous," meaning that the amount of drug in the crystalline form does not exceed about 10 wt %. Amounts of crystalline drug may be measured by powder X-ray diffraction, Scanning Electron Microscope (SEM) analysis, differential scanning calorimetry (DSC), or any other standard quantitative measurement.

The amorphous drug can exist as a pure phase, as a solid solution of drug homogeneously distributed throughout the polymer or any combination of these states or those states that lie intermediate between them. In cases where the drug is a low-solubility drug and concentration or bioavailability enhancement is desired, the dispersion is preferably "substantially homogeneous" so that the amorphous drug is dispersed as homogeneously as possible throughout the polymer. Dispersions of the present invention that are substantially homogeneous generally are more physically stable and have improved concentration-enhancing properties and, in turn improved bioavailability, relative to nonhomogeneous dispersions. As used herein, "substantially homogeneous" means that the drug present in relatively pure amorphous domains within the solid dispersion is relatively small, on the order of less than about 20%, and preferably less than about 10% of the total amount of drug. In a preferred embodiment, the dispersion comprises a solid solution of drug homogeneously distributed throughout the polymer.

In cases where the drug and the polymer have glass transition temperatures sufficiently far apart (greater than about 20° C.), the fraction of drug that is present in relatively pure amorphous drug domains or regions within the solid amorphous dispersion can be determined by examining the glass transition temperature ($T_g$) of the solid amorphous dispersion. $T_g$ as used herein is the characteristic temperature where a glassy material, upon gradual heating, undergoes a relatively rapid (e.g., in 10 to 100 seconds) physical change from a glassy state to a rubbery state. The $T_g$ of an amorphous material such as a polymer, drug, or dispersion can be measured by several techniques, including by a dynamic mechanical analyzer (DMA), a dilatometer, a dielectric analyzer, and by DSC. The exact values measured by each technique can vary somewhat, but usually fall within 100 to 30° C. of each other. When the solid amorphous dispersion exhibits a single $T_g$, the amount of drug in pure amorphous drug domains or regions in the solid amorphous dispersion is generally less than about 10 wt %, confirming that the solid amorphous dispersion is substantially homogeneous. This is in contrast to a simple physical mixture of pure amorphous drug particles and pure amorphous polymer particles which generally display two distinct $T_g$s, one being that of the drug and one that of the polymer. For a solid amorphous dispersion that exhibits two distinct $T_g$s, one in the proximity of the drug $T_g$ and one of the remaining drug/polymer dispersion, at least a portion of the drug is present in relatively pure amorphous domains. The amount of drug present in relatively pure amorphous drug domains or regions may be determined by first preparing calibration standards of substantially homogeneous dispersions to determine $T_g$ of the solid amorphous dispersion versus drug loading in the dispersion. From these calibration data and the $T_g$ of the drug/polymer dispersion, the fraction of drug in relatively pure amorphous drug domains or regions can be determined. Alternatively, the amount of drug present in relatively pure amorphous drug domains or regions may be determined by comparing the magnitude of the heat capacity for the transition in the proximity of the drug $T_g$ with calibration standards consisting essentially of a physical mixture of amorphous drug and polymer. In either case, a solid amorphous dispersion is considered to be substantially homogeneous if the fraction of drug that is present in relatively pure amorphous drug domains or regions within the solid amorphous dispersion is less than about 20 wt %, and preferably less than about 10 wt % of the total amount of drug.

To obtain the maximum level of concentration and bioavailability enhancement, particularly upon storage for long times prior to use, it is preferred that the drug remain, to the extent possible, in the amorphous state. The inventors have found that this is best achieved when the glass-transition temperature, $T_g$, of the amorphous dispersion is substantially above the storage temperature of the dispersion. In particular, it is preferable that the $T_g$ of the amorphous dispersion is at least about 40° C. and preferably at least about 60° C. Since the $T_g$ is a function of the water content of the dispersion which in turn is a function of the RH to which the dispersion is exposed, these $T_g$ values refer to the $T_g$ of the dispersion containing water in an amount that is in equilibrium with the RH equivalent to that found during storage. For those aspects of the invention in which the dispersion is a solid, substantially amorphous dispersion of drug in the polymer and in which the drug itself has a relatively low $T_g$ (about 70° C. or less) it is preferred that the dispersion polymer have a $T_g$ of at least about 40° C., preferably at least about 70° C. and more preferably greater than about 100° C. Since conversion of amorphous drug to the crystalline state is related to the relative values of (1) the $T_g$ of the dispersion (at the storage RH) and (2) the storage temperature, solid amorphous dispersions of the present invention may tend to remain in the amorphous state for longer periods when stored at relatively low temperatures and low relative humidities. In addition, packaging of such dispersions so as to prevent absorption of water or inclusion of a water absorbing material such as a desiccant to also prevent or retard water absorption can lead to a higher $T_g$ during storage, thereby helping to retain the amorphous state. Likewise, storage at lower temperatures can also improve the retention of the amorphous state.

Preparation of Solid Amorphous Dispersions

Solid amorphous dispersions of the invention may be made according to any known process that results in at least 60 wt % of the drug being in the amorphous state. Such processes include mechanical, thermal and solvent processes. Exemplary mechanical processes include milling and extrusion; melt processes include high temperature fusion, solvent modified fusion and melt-congeal processes; and solvent processes include non-solvent precipitation, spray coating and spray-drying. See, for example, U.S. Pat. No. 5,456,923 and U.S. Pat. No. 5,939,099 which describe formation of dispersions via extrusion processes; U.S. Pat. No. 5,340,591 and U.S. Pat. No. 4,673,564 which describe forming dispersions by milling processes; and U.S. Pat. No. 5,707,646 and U.S. Pat. No. 4,894,235 which describe the formation of dispersions via melt/congeal processes, the disclosures of which are incorporated by reference. In one embodiment, the process used to form the solid amorphous dispersion results in a substantially homogeneous dispersion, as described herein above.

When the drug has a relatively low melting point, typically less than about 200° C. and preferably less than about 160° C., extrusion or melt-congeal processes that provide heat and/or mechanical energy are often suitable for forming almost completely amorphous dispersions. For example, drug and polymer may be blended, with or without the addition of water, and the blend fed to a twin-screw extrusion device. The processing temperature may vary from about 50° C. up to about 200° C. depending on the melting point of the drug and polymer, which is a function of the degree of substitution on the polymer and the amount of water, if any, added. Generally, the higher the melting point of the drug and polymer, the higher the processing temperature. Generally, the lowest processing temperature that produces a satisfactory dispersion (almost completely amorphous and substantially homogeneous) is chosen.

Processes for forming solid amorphous dispersions using such thermal methods are described in more detail in commonly assigned copending U.S. patent application Ser. No. 10/066,091, the disclosure of which is incorporated herein by reference.

Another method for forming solid amorphous dispersions is by "solvent processing," which consists of dissolution of the drug and polymer in a common solvent. "Common" here means that the solvent, which can be a mixture of compounds, will dissolve both the drug and the polymer. After both the drug and the polymer have been dissolved, the solvent is rapidly removed by evaporation or by mixing with a non-solvent. Exemplary processes are spray-drying, spray-coating (pan-coating, fluidized bed coating, etc.), and precipitation by rapid mixing of the polymer and drug solution with $CO_2$, water, or some other non-solvent. Preferably, removal of the solvent results in the formation of a substantially homogeneous, solid amorphous dispersion. Solvent processes are preferred because they often allow the formation of substantially homogeneous, solid amorphous dispersions.

Solvents suitable for solvent processing can be any compound in which the drug and polymer are mutually soluble. Preferably, the solvent is also volatile with a boiling point of 150° C. or less. In addition, the solvent should have relatively low toxicity and be removed from the solid amorphous dispersion to a level that is acceptable according to The International Committee on Harmonization (ICH) guidelines. Removal of solvent to this level may require a subsequent processing step such as tray-drying. Preferred solvents include water; alcohols such as methanol and ethanol; ketones such as acetone, methyl ethyl ketone and methyl iso-butyl ketone; and various other solvents such as acetonitrile, methylene chloride and tetrahydrofuran. Lower volatility solvents such as dimethyl acetamide or dimethylsulfoxide can also be used. Mixtures of solvents, such as 50% methanol and 50% acetone, can also be used, as can mixtures with water, so long as the polymer and drug are sufficiently soluble to make the spray-drying process practicable. Generally, due to the hydrophobic nature of low-solubility drugs, non aqueous solvents are preferred, meaning that the solvent comprises less than about 30 wt % water.

One of the advantages of HPMCA is that it is soluble in more organic solvents than is HPMC. This allows for a wider selection of solvents that will dissolve both the drug and polymer. In addition, HPMCA tends to have a higher solubility in organic solvents than does HPMC, allowing the use of feed solutions containing higher percentages of polymer, improving process efficiency relative to HPMC.

A preferred method of removing the solvent is by spray-drying. The term "spray-drying" is used conventionally and broadly refers to processes involving breaking up liquid mixtures into small droplets (atomization) and rapidly removing solvent from the mixture in a spray-drying apparatus where there is a strong driving force for evaporation of solvent from the droplets. Spray-drying processes and spray-drying equipment are described generally in Perry's *Chemical Engineers' Handbook*, pages 20-54 to 20-57 (Sixth Edition 1984). More details on spray-drying processes and equipment are reviewed by Marshall, "Atomization and Spray-Drying," 50 *Chem. Eng. Prog. Monogr. Series* 2 (1954), and Masters, *Spray Drying Handbook* (Fourth Edition 1985). The strong driving force for solvent evaporation is generally provided by maintaining the partial pressure of solvent in the spray-drying apparatus well below the vapor pressure of the solvent at the temperature of the drying droplets. This is accomplished by (1) maintaining the pressure in the spray-drying apparatus at a partial vacuum (e.g., 0.01 to 0.50 atm); or (2) mixing the liquid droplets with a warm drying gas; or (3) both (1) and (2). In addition, at least a portion of the heat required for evaporation of solvent may be provided by heating the spray solution.

The solvent-bearing feed, comprising the drug and the polymer, can be spray-dried under a wide variety of conditions and yet still yield dispersions with acceptable properties. For example, various types of nozzles can be used to atomize the spray solution, thereby introducing the spray solution into the spray-dry chamber as a collection of small droplets. Essentially any type of nozzle may be used to spray the solution as long as the droplets that are formed are sufficiently small that they dry sufficiently (due to evaporation of solvent) that they do not stick to or coat the spray-drying chamber wall.

Although the maximum droplet size varies widely as a function of the size, shape and flow pattern within the spray-dryer, generally droplets should be less than about 500 μm in diameter when they exit the nozzle. Examples of types of nozzles that may be used to form the solid amorphous dispersions include the two-fluid nozzle, the fountain-type nozzle, the flat fan-type nozzle, the pressure nozzle and the rotary atomizer. In a preferred embodiment, a pressure nozzle is used, as disclosed in detail in commonly assigned copending U.S. application Ser. No. 10/351,568, the disclosure of which is incorporated herein by reference.

The spray solution can be delivered to the spray nozzle or nozzles at a wide range of temperatures and flow rates. Generally, the spray solution temperature can range anywhere from just above the solvent's freezing point to about 20° C. above its ambient pressure boiling point (by pressurizing the solution) and in some cases even higher. Spray solution flow rates to the spray nozzle can vary over a wide range depending on the type of nozzle, spray-dryer size and spray-dry conditions such as the inlet temperature and flow rate of the drying gas. Generally, the energy for evaporation of solvent from the spray solution in a spray-drying process comes primarily from the drying gas.

The drying gas can, in principle, be essentially any gas, but for safety reasons and to minimize undesirable oxidation of the drug or other materials in the solid amorphous dispersion, an inert gas such as nitrogen, nitrogen-enriched air or argon is utilized. The drying gas is typically introduced into the drying chamber at a temperature between about 600 and about 300° C. and preferably between about 800 and about 240° C.

The large surface-to-volume ratio of the droplets and the large driving force for evaporation of solvent leads to rapid solidification times for the droplets. Solidification times should be less than about 20 seconds, preferably less than about 10 seconds, and more preferably less than 1 second. This rapid solidification is often critical to the particles maintaining a uniform, homogeneous dispersion instead of separating into drug-rich and polymer-rich phases. In a preferred embodiment, the height and volume of the spray-dryer are adjusted to provide sufficient time for the droplets to dry prior to impinging on an internal surface of the spray-dryer, as described in detail in commonly assigned, copending U.S. application Ser. No. 10/353,746, incorporated herein by reference. As noted above, to get large enhancements in concentration and bioavailability it is often necessary to obtain as homogeneous a dispersion as possible.

Following solidification, the solid powder typically stays in the spray-drying chamber for about 5 to 60 seconds, further evaporating solvent from the solid powder. The final solvent content of the solid dispersion as it exits the dryer should be low, since this reduces the mobility of the drug molecules in the solid amorphous dispersion, thereby improving its stability. Generally, the solvent content of the solid amorphous dispersion as it leaves the spray-drying chamber should be less than 10 wt % and preferably less than 2 wt %. Following formation, the solid amorphous dispersion can be dried to remove residual solvent using suitable drying processes, such as tray drying, fluid bed drying, microwave drying, belt drying, rotary drying, vacuum drying, and other drying processes known in the art.

Spray-drying processes and spray-drying equipment are described generally in Perry's *Chemical Engineers' Handbook*, Sixth Edition (R. H. Perry, D. W. Green, J. O. Maloney, eds.) McGraw-Hill Book Co. 1984, pages 20-54 to 20-57. More details on spray-drying processes and equipment are reviewed by Marshall "Atomization and Spray-Drying," 50 *Chem. Eng. Prog. Monogr. Series* 2 (1954).

The solid amorphous dispersion is usually in the form of small particles. The mean size of the particles may be less than 500 μm in diameter, or less than 100 μm in diameter, less than 50 μm in diameter or less than 25 μm in diameter. When the solid amorphous dispersion is formed by spray-drying, the resulting dispersion is in the form of such small particles. When the solid amorphous dispersion is formed by other methods such by melt-congeal or extrusion processes, the resulting dispersion may be sieved, ground, or otherwise processed to yield a plurality of small particles.

Once the solid amorphous dispersion comprising the drug and polymer has been formed, several processing operations can be used to facilitate incorporation of the dispersion into a dosage form. These processing operations include drying, granulation, and milling.

The solid amorphous dispersion may be granulated to increase particle size and improve handling of the dispersion while forming a suitable dosage form. Preferably, the average size of the granules will range from 50 to 1000 μm. Such granulation processes may be performed before or after the composition is dried, as described above. Dry or wet granulation processes can be used for this purpose. An example of a dry granulation process is roller compaction. Wet granulation processes can include so-called low shear and high shear granulation, as well as fluid bed granulation. In these processes, a granulation fluid is mixed with the composition after the dry components have been blended to aid in the formation of the granulated composition. Examples of granulation fluids include water, ethanol, isopropyl alcohol, n-propanol, the various isomers of butanol, and mixtures thereof. A polymer may be added with the granulation fluid to aid in granulating the dispersion. Examples of suitable polymers include more concentration-enhancing polymer, hydroxypropyl cellulose, hydroxyethyl cellulose, and hydroxypropyl methylcellulose.

If a wet granulation process is used, the granulated composition is often dried prior to further processing. Examples of suitable drying processes to be used in connection with wet granulation are the same as those described above. Where the solid amorphous dispersion is made by a solvent process, the composition can be granulated prior to removal of residual solvent. During the drying process, residual solvent and granulation fluid are concurrently removed from the composition.

Once the composition has been granulated, it may then be milled to achieve the desired particle size. Examples of suitable processes for milling the composition include hammer milling, ball milling, fluid-energy milling, roller milling, cutting milling, and other milling processes known in the art.

Physical Stability

Solid amorphous dispersions comprising a low-solubility drug and a polymer of the present invention generally have improved physical stability. As used herein, "physical stability" or "physically stable" means either (1) the tendency of the amorphous drug present in the dispersion to crystallize or (2) when the dispersion is substantially homogeneous, the tendency of the drug to separate into drug-rich domains—the drug in the drug-rich domains being amorphous or crystalline. Thus, a dispersion that is more physically stable than another will have either (1) a slower rate of drug crystallization in the dispersion, or (2) a slower rate of formation of drug-rich domains. Specifically, solid amorphous dispersions of the present invention have sufficient stability that less than about 10 wt % of the drug in the dispersion crystallizes during storage for 3 weeks at 25° C. and 10% RH. Preferably, less than 5 wt % of the drug crystallizes during storage for 3 weeks at 25° C. and 10% RH.

Without wishing to be bound by any particular theory or mechanism of action, it is believed that solid amorphous dispersions generally fall into two categories with respect to physical stability: (1) those that are thermodynamically stable (in which there is little or no driving force for crystallization of the amorphous drug in the dispersion) and (2) those that are kinetically stable or metastable (in which driving force exists for crystallization of the amorphous drug but low drug mobility slows the rate of crystallization to an acceptable level).

For thermodynamically stable dispersions, the solubility of the amorphous drug in the polymer should be approximately equal to or greater than the drug loading. By drug loading is meant the weight fraction of drug in the solid amorphous dispersion. The drug loading can be slightly higher (that is, 10% to 20% higher) than the solubility and still be physically stable as the driving force for crystal nucleation is quite low.

The inventors have discovered that for low-solubility drugs, and in particular, for hydrophobic drugs, the solubility of the amorphous form of the drug in the polymer is related to the difference between (1) the solubility parameter of the drug and (2) the solubility parameter of the polymer. Without wishing to be bound by any particular theory or mechanism of action, it is believed that the smaller the difference between the solubility parameter of the drug and the solubility parameter of the polymer, the higher the solubility of the drug in the polymer. As the difference between the solubility parameter of the drug and the solubility parameter of the polymer is decreased, the solubility of the drug in the polymer is increased. The physical stability of a solid amorphous dispersion in turn, increases as the solubility of the drug in the polymer increases.

Thus, in one embodiment, the HPMCA polymer has a solubility parameter of about 24.0 $(J/cm^3)^{1/2}$ or less. Preferably, the HPMCA polymer has a solubility parameter of about 23.8 $(J/cm^3)^{1/2}$ or less, and more preferably, about 23.6 $(J/cm^3)^{1/2}$ or less. Procedures for calculating the solubility parameter of a drug and HPMCA are outlined herein below.

Specifically, the inventors have found that the solubility of a low solubility drug (having a solubility parameter $\delta_D$) in HPMCAS (having a solubility parameter $\delta_P$) is generally less than about 25 wt % when $(\delta_D-\delta_P)^2$ is about 2 or greater and the melting point of the drug is about 100° C. or more. As a result, solid amorphous dispersions made with a high drug loading (that is, greater than about 25 wt % drug) wherein the solubility parameter difference $((\delta_D-\delta_P)^2)$ is about 2.0 or greater, generally are not thermodynamically stable. If the dispersion is not kinetically stable (as discussed below), the drug can phase separate over time. Thus, in one embodiment, it is preferred that $(\delta_D-\delta_P)^2$ is less than about 2, more preferably less than about 1.8, and even more preferably less than about 1.5. The inventors have found that solid amorphous dispersions that satisfy this relationship can have higher drug loadings and have better thermodynamically stability than dispersions that do not satisfy this relationship.

When the drug loading in the dispersion is ten to twenty percent greater than the solubility of the drug in the polymer (that is, the dispersion is supersaturated in drug), the dispersion is not thermodynamically stable and a driving force exists for phase separation of the amorphous drug in the dispersion into a drug-rich phase. Such drug-rich phases may be amorphous and microscopic (less than about 1 μm in size), amorphous and relatively large (greater than about 1 μm in size), or crystalline in nature. Following phase separation, the dispersion can consist of two phases: (1) a drug-rich phase comprising primarily drug, and (2) a second phase comprising amorphous drug dispersed in the polymer. The amorphous drug in the drug-rich phase can over time convert from the amorphous form to the lower-energy crystalline form. The physical stability of such dispersions will generally be greater, for a given drug loading, (1) the lower the molecular mobility of the amorphous drug, and (2) the lower the tendency for the amorphous drug to crystallize from the drug-rich phases.

Molecular mobility is generally lower and physical stability greater for dispersions with high $T_g$ values. The $T_g$ of the dispersion is an indirect measure of the molecular mobility of the drug in the dispersion. The higher the $T_g$, the lower the mobility. Thus, the ratio of the $T_g$ to storage temperature ($T_{storage}$) for the dispersion (in K) is an accurate indicator of the relative drug mobility at a given storage temperature. In order to minimize phase separation, it is desired that the mobility of the amorphous drug in the dispersion be low. This is accomplished by maintaining a ratio of $T_g/T_{storage}$ of greater than about 1. Since typical storage temperatures can range anywhere from 5° C. to 40° C. at moderate humidity (typically at a relative humidity (RH) of about 20% to 75%), it is preferred that the $T_g$ of the dispersion at 50% RH be at least about 30° C., more preferably at least about 40° C., and most preferably at least about 50° C.

The $T_g$ of a solid amorphous dispersion depends on several factors, including (1) the $T_g$ of the polymer, (2) the $T_g$ of the low-solubility drug, and (3) the relative amounts of polymer and drug in the dispersions. The $T_g$ for a homogeneous blend of two amorphous materials with similar densities (as is roughly the case for many drugs and polymers) can be estimated from the Gordon-Taylor Equation (M. Gordon, and J. S. Taylor, J. of Applied Chem., 2, 493-500, 1952) as follows:

$$T_{g,1,2} = \frac{w_1 T_{g1} + K w_w T_{g2}}{w_1 + K w_2}$$

where $w_1$ and $w_2$ are the weight fractions of the components 1 and 2, $T_{g1}$ and $T_{g2}$ are the glass-transition temperatures of components 1 and 2, respectively, $T_{g,1,2}$ is the glass-transition temperature of the mixture of components 1 and 2, and K is a constant related to the free volumes of the two components. Thus, for a given low-solubility drug, the greater the $T_g$ of the polymer, the greater the weight fraction of drug that can be in the dispersion while maintaining a $T_g$ for the dispersion of greater than about 30° C.

The inventors have found that the novel HPMCAS polymers of the present invention have $T_g$ values of at least about 80° C. at 50% RH, and typically at least about 90° C. at 50% RH. Thus, depending on the drug loading, solid amorphous dispersions comprising a low-solubility drug and an HPMCAS polymer of the present invention having such high $T_g$ values are generally kinetically stable.

The inventors have found that the novel HPMCA polymers of the present invention have $T_g$ values of at least about 100° C. at 50% RH. This is in contrast to HPMC, which has a $T_g$ value of about 96° C. at 50% RH. Thus, depending on the drug loading, solid amorphous dispersions comprising a drug and an HPMCA polymer of the present invention having such high $T_g$ values are generally kinetically stable.

In another embodiment, a solid amorphous dispersion made using a low-solubility drug and an HPMCAS polymer of the present invention provides improved physical stability relative to a control composition. The control composition used to evaluate physical stability consists essentially of a solid amorphous dispersion of an equivalent amount of drug in an equivalent amount of HPMCAS, but wherein the HPMCAS is a commercial grade of HPMCAS (e.g., either the AQOAT "L" grade, "M" grade, or "H" grade).

In one aspect, an improvement in physical stability may be determined by comparing the rate of crystallization of the drug in a "test composition" comprising a drug and a polymer of the present invention, with the rate of crystallization of drug in the control composition. The rate of crystallization of drug may be measured by determining the fraction of drug in the crystalline state in the test composition or control composition over time in a typical storage environment. This may be measured by any standard physical measurement, such as x-ray diffraction, DSC, solid state NMR or Scanning Electron Microscope ("SEM") analysis. Drug in a physically stable test composition will crystallize at a slower rate than the drug in the control composition. Preferably, the rate of crystallization of the drug in the test composition is less than 90%, and more preferably less than 80%, of the rate of crystallization of drug in the control composition. Thus, for example, if the drug in the control composition crystallizes at a rate of 1%/week, the drug in the test composition crystallizes at a rate of less than 0.9%/week. Often, much more dramatic improvements are observed, such as less than about 10% of the rate of crystallization of drug in the control composition (or less than about 0.1%/week for the example given).

In another aspect, an improvement in physical stability may be determined by comparing the rate of phase separation of drug from the drug/polymer dispersion of the test composition and the control composition. By "rate of phase separation" is meant the rate at which the drug, originally present as a homogeneous dispersion of amorphous drug in the polymer, separates into drug-rich amorphous regions. The rate of phase separation of drug from the dispersion may be measured using the procedures previously discussed. Preferably, the rate of phase separation of the drug in the test composition is less than 90%, and more preferably less than 80%, of the rate of phase separation of drug in the control composition.

Improvement in physical stability may be determined by comparing the rate of phase separation of the drug in a "test composition" comprising a drug and a polymer of the present invention, with the rate of phase separation of drug in the control composition. The rate of phase separation of drug may be measured using a differential scanning calorimetry (DSC) analysis of the dispersion. DSC analysis of a composition that has phase separated drug regions will display two glass-transition temperatures ($T_g$s): (1) one that is close or the same as that of pure amorphous drug, corresponding to the phase separated drug, and (2) one that is substantially higher than that of the drug, corresponding to the dispersion from which the drug has phase separated. The amount of phase separated drug present may be determined by comparing the magnitude of the thermal event corresponding to the phase separated drug (i.e., the heat capacity) with standards of amorphous drug alone.

A relative degree of improvement in physical stability may be used to characterize the improvement in physical stability obtained by the compositions of the present invention. The "relative degree of improvement in physical stability" is defined as the ratio of (1) the rate of drug crystallization or phase separation in the control composition and (2) the rate of drug crystallization or phase separation in the test composition. For example, if the drug in the control composition phase separates at a rate of 10 wt %/week and the drug in the test composition phase separates at a rate of 5 wt %/week, the relative degree of improvement in physical stability would be 2 (10 wt %/week÷5 wt %/week). Preferably, the compositions of the present invention provide a relative degree of improvement in physical stability of at least 1.25, preferably 2.0, more preferably 3.0 relative to a control composition consisting essentially of an equivalent amount of drug and an equivalent amount of polymer, but wherein the polymer is a commercial grade. Preferably the commercial grade of HPMCAS polymer used in the control composition is the HPMCAS-M grade available from Shin Etsu and for the HPMCA polymer, the E3 Prem LV grade of HPMC (Dow Chemical Co., Midland, Mich.).

The particular storage conditions and time of storage to evaluate physical stability may be chosen as convenient. A stability test which may be used to test whether a composition meets the stability criteria described above is storage of the test composition and the control composition for six months at 40° C. and 75% RH. An improvement of stability for the test composition may become apparent within a shorter time, such as three to five days, and shorter storage times may be used for some drugs. When comparing compositions under storage conditions which approximate ambient conditions, e.g., 25° C. and 60% RH, the storage period may need to be from several months up to two years.

The improvement in physical stability for the compositions of the present invention allows formation of solid amorphous dispersions with a higher drug loading (e.g., higher drug:polymer ratio) while still retaining good physical stability. That is, compositions comprising drug and polymer wherein the difference in solubility parameter of the drug and the polymer meet the criteria outlined herein may contain a greater proportion of drug than a solid amorphous dispersion that does not meet the criteria while still retaining good physical stability.

Concentration Enhancement

In another separate embodiment, the compositions of the present invention are concentration enhancing. The term "concentration enhancing" means that the polymer is present in a sufficient amount in the composition so as to improve the concentration of dissolved drug in an aqueous use environment relative to a control composition free from the polymer. As used herein, a "use environment" can be either the in vivo environment of the GI tract, subdermal, intranasal, buccal, intrathecal, ocular, intraaural, subcutaneous spaces, vaginal tract, arterial and venous blood vessels, pulmonary tract or intramuscular tissue of an animal, such as a mammal and particularly a human, or the in vitro environment of a test solution, such as phosphate buffered saline (PBS), simulated intestinal buffer without enzymes (SIN), a Model Fasted Duodenal (MFD) solution, or a solution to model the fed state. Concentration enhancement may be determined through either in vitro dissolution tests or through in vivo tests. It has been determined that enhanced drug concentration in in vitro dissolution tests in such in vitro test solutions provide good indicators of in vivo performance and bioavailability. An appropriate PBS solution is an aqueous solution comprising 20 mM sodium phosphate ($Na_2HPO_4$), 47 mM potassium phosphate ($KH_2PO_4$), 87 mM NaCl, and 0.2 mM KCl, adjusted to pH 6.5 with NaOH. An appropriate SIN solution is 50 mM $KH_2PO_4$ adjusted to pH 7.4. An appropriate MFD solution is the same PBS solution wherein additionally is present 7.3 mM sodium taurocholic acid and 1.4 mM of 1-palmitoyl-2-oleyl-sn-glycero-3-phosphocholine. An appropriate solution to model the fed state is the same PBS solution wherein additionally is present 29.2 mM sodium taurocholic acid and 5.6 mM of 1-palmitoyl-2-oleyl-sn-glycero-3-phosphocholine. In particular, a composition of the present invention may be dissolution-tested by adding it to an in vitro test solution and agitating to promote dissolution, or by performing a membrane-permeation test as described herein.

In one aspect, a composition of the present invention, when dosed to an aqueous use environment, provides a maximum drug concentration (MDC) that is at least 1.25-fold the MDC provided by a control composition. In other words, if the MDC provided by the control composition is 100 μg/mL, then a composition of the present invention containing a concentration-enhancing polymer provides an MDC of at least 125 μg/mL. More preferably, the MDC of drug achieved with the compositions of the present invention are at least 2-fold, even more preferably at least 3-fold, and most preferably at least 5-fold that of the control composition. Surprisingly, the compositions may achieve extremely large enhancements in aqueous concentration. In some cases, the MDC of very hydrophobic drugs provided by the compositions of the present invention are at least 10-fold, at least 50-fold, at least 200-fold, at least 500-fold, to more than 1000-fold that of the control composition.

The control composition is conventionally the undispersed drug alone (e.g., typically, the crystalline drug alone in its most thermodynamically stable crystalline form, or in cases where a crystalline form of the drug is unknown, the control may be the amorphous drug alone) or the drug plus a weight of inert diluent equivalent to the weight of polymer in the test composition. By inert is meant that the diluent is not concentration enhancing.

Alternatively, the compositions of the present invention provide in an aqueous use environment a concentration versus time Area Under the Curve (AUC), for any period of at least 90 minutes between the time of introduction into the use environment and about 270 minutes following introduction to the use environment that is at least 1.25-fold that of the control composition. More preferably, the AUC in the aqueous use environment achieved with the compositions of the present invention are at least 2-fold, more preferably at least 3-fold, and most preferably at least 5-fold that of a control composition. For some hydrophobic drugs, the compositions may provide an AUC value that is at least 10-fold, at least 25-fold, at least 100-fold, and even more than 250-fold that of the control described above.

Alternatively, the compositions of the present invention, when dosed orally to a human or other animal, provide an AUC in drug concentration in the blood plasma or serum that is at least 1.25-fold that observed when an appropriate control composition is dosed. Preferably, the blood AUC is at least about 2-fold, preferably at least about 3-fold, preferably at least about 4-fold, preferably at least about 6-fold, preferably at least about 10-fold, and even more preferably at least about 20-fold that of the control composition. It is noted that such compositions can also be said to have a relative bioavailability of from about 1.25-fold to about 20-fold that of the control composition. Thus, the compositions that, when evaluated, meet either the in vitro or the in vivo, or both, performance criteria are a part of this invention.

Alternatively, the compositions of the present invention, when dosed orally to a human or other animal, provide maximum drug concentration in the blood plasma or serum ($C_{max}$) that is at least 1.25-fold that observed when an appropriate control composition is dosed. Preferably, the blood $C_{max}$ is at least about 2-fold, preferably at least about 3-fold, preferably at least about 4-fold, preferably at least about 6-fold, preferably at least about 10-fold, and even more preferably at least about 20-fold that of the control composition.

A typical in vitro test to evaluate enhanced drug concentration can be conducted by (1) administering with agitation a sufficient quantity of test composition (that is, the dispersion of the low-solubility, acid-sensitive, or hydrophobic drug and polymer) in a test medium, such that if all of the drug dissolved, the theoretical concentration of drug would exceed the equilibrium concentration of the drug by a factor of at least 2; (2) in a separate test, adding an appropriate amount of control composition to an equivalent amount of test medium; and (3) determining whether the measured MDC and/or AUC of the test composition in the test medium is at least 1.25-fold that provided by the control composition. In conducting such a dissolution test, the amount of test composition or control composition used is an amount such that if all of the drug dissolved, the drug concentration would be at least 2-fold, preferably at least 10-fold, and most preferably at least 100-fold that of the aqueous solubility (that is, the equilibrium concentration) of the drug. For some test compositions of a very low-solubility drug and polymer, it may be necessary to administer an even greater amount of the test composition to determine the MDC.

The concentration of dissolved drug is typically measured as a function of time by sampling the test medium and plotting drug concentration in the test medium vs. time so that the MDC and/or AUC can be ascertained. The MDC is taken to be the maximum value of dissolved drug measured over the duration of the test. The aqueous AUC is calculated by integrating the concentration versus time curve over any 90-minute time period between the time of introduction of the composition into the aqueous use environment (when time equals zero) and 270 minutes following introduction to the use environment (when time equals 270 minutes). Typically, when the composition reaches its MDC rapidly, in say less than about 30 minutes, the time interval used to calculate AUC is from time equals zero to time equals 90 minutes. However, if the AUC of a composition over any 90-minute time period described above meets the criterion of this invention, then the composition formed is considered to be within the scope of this invention.

To avoid drug particulates that would give an erroneous determination, the test solution is either filtered or centrifuged. "Dissolved drug" is typically taken as that material that either passes a 0.45 µm syringe filter or, alternatively, the material that remains in the supernatant following centrifugation. Filtration can be conducted using a 13 mm, 0.45 µm polyvinylidine difluoride syringe filter sold by Scientific Resources under the trademark TITAN®. Centrifugation is typically carried out in a polypropylene microcentrifuge tube by centrifuging at 13,000 G for 60 seconds. Other similar filtration or centrifugation methods can be employed and useful results obtained. For example, using other types of microfilters may yield values somewhat higher or lower (±10-40%) than that obtained with the filter specified above but will still allow identification of preferred dispersions. It is recognized that this definition of "dissolved drug" encompasses not only monomeric solvated drug molecules but also a wide range of species such as polymer/drug assemblies that have submicron dimensions such as drug aggregates, aggregates of mixtures of polymer and drug, micelles, polymeric micelles, colloidal particles or nanocrystals, polymer/drug complexes, and other such drug-containing species that are present in the filtrate or supernatant in the specified dissolution test.

An in vitro membrane-permeation test may also be used to evaluate the compositions of the present invention, described in detail in the Examples section.

Further details of this membrane-permeation test are presented in co-pending U.S. Provisional Patent Application Ser. No. 60/557,897, entitled "Method and Device for Evaluation of Pharmaceutical Compositions," filed Mar. 30, 2004, incorporated herein by reference.

In general terms, a typical in vitro membrane-permeation test to evaluate enhanced drug concentration can be conducted by providing a drug-permeable membrane between feed and permeate reservoirs, as described in detail in the Examples, then (1) administering a sufficient quantity of test composition (that is, the composition of the low-solubility, acid-sensitive, or hydrophobic drug and polymer) to a feed solution, such that if all of the drug dissolved, the theoretical concentration of drug would exceed the equilibrium concentration of the drug by a factor of at least 2; (2) in a separate test, adding an equivalent amount of control composition to an equivalent amount of test medium; and (3) determining whether the measured maximum flux of drug provided by the test composition is at least 1.25-fold that provided by the control composition. A composition of the present invention provides concentration enhancement if, when dosed to an aqueous use environment, it provides a maximum flux of drug in the above test that is at least about 1.25-fold the maximum flux provided by the control composition. Preferably, the maximum flux provided by the compositions of the present invention are at least about 1.5-fold, more preferably at least about 2-fold, and even more preferably at least about 3-fold that provided by the control composition.

Alternatively, the compositions of the present invention, when dosed orally to a human or other animal, results in improved bioavailability or $C_{max}$. Relative bioavailability and $C_{max}$ of drugs in the compositions can be tested in vivo in animals or humans using conventional methods for making such a determination. An in vivo test, such as a crossover study, may be used to determine whether a composition of drug and polymer provides an enhanced relative bioavailability or $C_{max}$ compared with a control composition as described above. In an in vivo crossover study a test composition comprising a low-solubility drug and polymer is dosed to half a group of test subjects and, after an appropriate washout period (e.g., one week) the same subjects are dosed with a control composition that consists of an equivalent quantity of crystalline drug as the test composition (but with no polymer present). The other half of the group is dosed with the control composition first, followed by the test composition. The relative bioavailability is measured as the concentration of drug in the blood (serum or plasma) versus time area under the curve (AUC) determined for the test group divided by the AUC in the blood provided by the control composition. Preferably, this test/control ratio is determined for each subject, and then the ratios are averaged over all subjects in the study. In vivo determinations of AUC and $C_{max}$ can be made by plotting the serum or plasma concentration of drug along the ordinate (y-axis) against time along the abscissa (x-axis). To facilitate dosing, a dosing vehicle may be used to administer the dose. The dosing vehicle is preferably water, but may also contain materials for suspending the test or control composition, provided these materials do not dissolve the composition or change the aqueous solubility of the drug in vivo. The determination of AUCs and $C_{max}$ is a well-known procedure and is described, for example, in Welling, "Pharmacokinetics Processes and Mathematics," ACS Monograph 185 (1986).

Excipients and Dosage Forms

The inclusion of other excipients in the composition may be useful in order to formulate the composition into tablets, capsules, suspensions, powders for suspension, creams, transdermal patches, depots, and the like. The composition of drug and polymer can be added to other dosage form ingredients in essentially any manner that does not substantially alter the drug. When the composition of the present invention is in the form of a solid amorphous dispersion, the excipients may be either physically mixed with the dispersion and/or included within the dispersion.

One very useful class of excipients is surfactants. Suitable surfactants include fatty acid and alkyl sulfonates, such as sodium lauryl sulfate; commercial surfactants such as benzalkonium chloride (HYAMINE® 1622, available from Lonza, Inc., Fairlawn, N.J.); dioctyl sodium sulfosuccinate, DOCUSATE SODIUM™ (available from Mallinckrodt Spec. Chem., St. Louis, Mo.); polyoxyethylene sorbitan fatty acid esters (TWEEN®, available from ICI Americas Inc., Wilmington, Del.; LIPOSORB® P-20 available from Lipochem Inc., Patterson N.J.; CAPMUL® POE-0 available from Abitec Corp., Janesville, Wis.); natural surfactants such as sodium taurocholic acid, 1-palmitoyl-2-oleoyl-sn-glycero-3-phosphocholine, lecithin, and other phospholipids and mono- and diglycerides; and polyoxyethylene-polyoxypropylene block copolymers, also known as poloxamers. Such materials can advantageously be employed to increase the rate of dissolution by facilitating wetting, thereby increasing the maximum dissolved concentration, and also to inhibit crystallization or precipitation of drug by interacting with the dissolved drug by mechanisms such as complexation, formation of inclusion complexes, formation of micelles or adsorbing to the surface of solid drug, crystalline or amorphous. These surfactants may comprise up to about 5 wt % of the composition.

The inclusion of pH modifiers such as acids, bases, or buffers may also be beneficial, retarding the dissolution of the composition (e.g., acids such as citric acid or succinic acid) or, alternatively, enhancing the rate of dissolution of the composition (e.g., bases such as sodium acetate or amines).

Other conventional formulation excipients may be employed in the compositions of this invention, including those excipients well-known in the art (e.g., as described in *Remington: The Science and Practice of Pharmacy* (20$^{th}$ ed., 2000). Generally, excipients such as fillers, disintegrating agents, pigments, binders, lubricants, glidants, flavorants, and so forth may be used for customary purposes and in typical amounts without adversely affecting the properties of the compositions. These excipients may be utilized after the drug/polymer composition has been formed, in order to formulate the composition into tablets, capsules, suppositories, suspensions, powders for suspension, creams, transdermal patches, depots, and the like.

Examples of other matrix materials, fillers, or diluents include lactose, mannitol, xylitol, dextrose, sucrose, sorbitol, compressible sugar, microcrystalline cellulose, powdered cellulose, starch, pregelatinized starch, dextrates, dextran, dextrin, dextrose, maltodextrin, calcium carbonate, dibasic calcium phosphate, tribasic calcium phosphate, calcium sulfate, magnesium carbonate, magnesium oxide, poloxamers such as polyethylene oxide, and hydroxypropyl methyl cellulose.

Examples of drug complexing agents or solubilizers include the polyethylene glycols, caffeine, xanthene, gentisic acid and cyclodextrins.

Examples of disintegrants include sodium starch glycolate, sodium carboxymethyl cellulose, calcium carboxymethyl cellulose, croscarmellose sodium, crospovidone (polyvinylpolypyrrolidone), methylcellulose, microcrystalline cellulose, powdered cellulose, starch, pregelatinized starch, and sodium alginate.

Examples of tablet binders include acacia, alginic acid, carbomer, carboxymethyl cellulose sodium, dextrin, ethylcellulose, gelatin, guar gum, hydrogenated vegetable oil, hydroxyethyl cellulose, hydroxypropyl cellulose, hydroxypropyl methyl cellulose, methyl cellulose, liquid glucose, maltodextrin, polymethacrylates, povidone, pregelatinized starch, sodium alginate, starch, sucrose, tragacanth, and zein.

Examples of lubricants include calcium stearate, glyceryl monostearate, glyceryl palmitostearate, hydrogenated vegetable oil, light mineral oil, magnesium stearate, mineral oil, polyethylene glycol, sodium benzoate, sodium lauryl sulfate, sodium stearyl fumarate, stearic acid, talc, and zinc stearate.

Examples of glidants include silicon dioxide, talc and cornstarch.

The compositions of the present invention may be delivered by a wide variety of routes, including, but not limited to, oral, nasal, rectal, vaginal, subcutaneous, intravenous and pulmonary. Generally, the oral route is preferred.

Compositions of this invention may also be used in a wide variety of dosage forms for administration of drugs. Exemplary dosage forms are powders or granules that may be taken orally either dry or reconstituted by addition of water or other liquids to form a paste, slurry, suspension or solution; tablets; capsules; multiparticulates; and pills. Various additives may be mixed, ground, or granulated with the compositions of this invention to form a material suitable for the above dosage forms.

The compositions of the present invention may be formulated in various forms such that they are delivered as a suspension of particles in a liquid vehicle. Such suspensions may be formulated as a liquid or paste at the time of manufacture, or they may be formulated as a dry powder with a liquid, typically water, added at a later time but prior to oral administration. Such powders that are constituted into a suspension are often termed sachets or oral powder for constitution (OPC) formulations. Such dosage forms can be formulated and reconstituted via any known procedure. The simplest approach is to formulate the dosage form as a dry powder that is reconstituted by simply adding water and agitating. Alternatively, the dosage form may be formulated as a liquid and a dry powder that are combined and agitated to form the oral suspension. In yet another embodiment, the dosage form can be formulated as two powders that are reconstituted by first adding water to one powder to form a solution to which the second powder is combined with agitation to form the suspension.

Generally, it is preferred that the dispersion of drug be formulated for long-term storage in the dry state as this promotes the chemical and physical stability of the drug.

Other features and embodiments of the invention will become apparent from the following examples that are given for illustration of the invention rather than for limiting its intended scope.

EXAMPLES

Comparative Example 1

Several lots of AQOAT polymers of various grades were purchased from Shin Etsu (Tokyo, Japan). The certificate of analysis for each lot gave the weight percentage of methoxyl, hydroxypropoxyl, acetyl, and succinoyl substituents on the polymer. From these data the degree of substitution of the various substituents was calculated using the procedures outlined herein. Table I shows the range and average values of the manufacturer's certificates of analysis for the various grades and the range and average values of the calculated degree of substitution for the various grades of polymers. In addition, FIG. 1 shows a plot of $DOS_S$ versus $DOS_{Ac}$ for the various grades and lots of AQOAT polymers evaluated.

Using these calculated degrees of substitution, the solubility parameter for the polymer, based on the average degree of substitution on the polymer, was calculated using the methods described herein. The results of these calculations are also shown in Table I. Also shown in Table I is the $T_g$ of the polymer measured at 50% RH by DSC.

mentation methods. The $T_g$ of amorphous Drug 2 was determined by DSC analysis to be 46° C. The solubility parameter of Drug 2 was calculated using the procedure outlined above to be 20.35 $(J/cm^3)^{1/2}$.

TABLE I

| | | L Grades | | M Grades | | H Grades | |
|---|---|---|---|---|---|---|---|
| Item | Substituent | Range | Average (of 12 lots) | Range | Average (of 28 lots) | Range | Average (of 17 lots) |
| Manufacturer's | Methoxyl | 21.7-22.5 | 22.1 ± 0.3 | 22.7-23.6 | 23.1 ± 0.2 | 23.2-24.1 | 23.7 ± 0.3 |
| Certificate of | Hydroxypropoxyl | 6.8-7.1 | 7.0 ± 0.1 | 7.0-7.9 | 7.3 ± 0.2 | 7.1-7.8 | 7.5 ± 0.2 |
| Analysis | Acetyl | 7.2-8.1 | 7.7 ± 0.3 | 8.7-10.8 | 9.3 ± 0.4 | 11.0-12.2 | 11.5 ± 0.3 |
| (wt %) | Succinoyl | 15.1-16.5 | 15.5 ± 0.4 | 10.8-11.5 | 11.2 ± 0.2 | 5.3-7.6 | 6.5 ± 0.7 |
| Calculated | $DOS_M$ | 1.84-1.91 | 1.87 ± 0.03 | 1.85-1.94 | 1.89 ± 0.02 | 1.84-1.92 | 1.88 ± 0.02 |
| Degree of | $DOS_{HP}$ | 0.24-0.25 | 0.25 ± 0.01 | 0.24-0.27 | 0.25 ± 0.01 | 0.23-0.26 | 0.24 ± 0.01 |
| Substitution | $DOS_{Ac}$ | 0.44-0.49 | 0.47 ± 0.02 | 0.51-0.65 | 0.55 ± 0.03 | 0.62-0.70 | 0.66 ± 0.02 |
| | $DOS_S$ | 0.39-0.43 | 0.40 ± 0.01 | 0.27-0.29 | 0.28 ± 0.01 | 0.13-0.19 | 0.16 ± 0.02 |
| | $DOS_M + DOS_{Ac} + DOS_S$ | 2.70-2.80 | 2.75 ± 0.03 | 2.65-2.87 | 2.71 ± 0.03 | 2.63-2.73 | 2.70 ± 0.03 |
| | $DOS_{Ac} + DOS_S$ | 0.85-0.89 | 0.88 ± 0.01 | 0.80-0.93 | 0.83 ± 0.03 | 0.77-0.84 | 0.81 ± 0.02 |
| Solubility Parameter $(J/cm^3)^{1/2}$ | | 22.75 | | 22.20 | | 21.99 | |
| $T_g$ (° C. at 50% RH) | | 94 | | 101 | | 98 | |

Drugs Used in Examples

The following drugs were used in the examples as described below.

Drug 1 was [2R,4S]-4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester, also known as torcetrapib, having the structure:

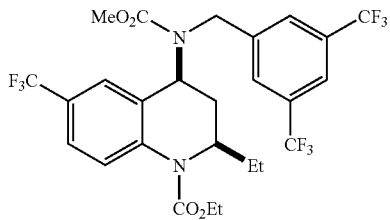

Torcetrapib has a solubility in water of less than 0.1 µg/mL, and a Log P value of 7.0, as determined by the average value estimated using Crippen's, Viswanadhan's, and Broto's fragmentation methods. The $T_g$ of amorphous Drug 1 was determined by DSC analysis to be 29° C. As previously discussed, torcetrapib has a solubility parameter of 20.66 $(J/cm^3)^{1/2}$.

Drug 2 was [2R,4S]-4-[acetyl-(3,5-bis-trifluoromethyl-benzyl)-amino]-2-ethyl-6-trifluoromethyl-3,4-dihydro-2H-quinoline-1-carboxylic acid isopropyl ester, having the structure:

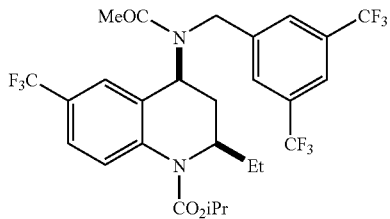

Drug 2 has a solubility in water of less than 1 µg/mL, and a Log P value of 6.7, as determined by the average value estimated using Crippen's, Viswanadhan's, and Broto's frag- Drug 3 was [2R,4S]-4-[(3,5-bis-trifluoromethyl-benzyl)-methoxycarbonyl-amino]-2-ethyl-6-trifluoromethyl-3,4-dihydro-2H-quinoline-1-carboxylic acid isopropyl ester, having the structure:

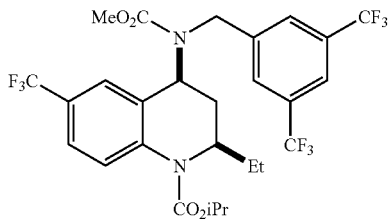

Drug 3 has a solubility in water of less than 1 µg/mL, and a Log P value of 7.8, as determined by the average value estimated using Crippen's, Viswanadhan's, and Broto's fragmentation methods. The $T_g$ of amorphous Drug 3 was determined by DSC analysis to be 30° C. The solubility parameter of Drug 3 was calculated using the procedure outlined above to be 20.45 $(J/cm^3)^{1/2}$.

Drug 4 was (2R)-3-[[3-(4-chloro-3-ethylphenoxy)phenyl][[3-(1,1,2,2-tetrafluoroethoxy)phenyl]methyl]amino]-1,1,1-trifluoro-2-propanol, having the structure:

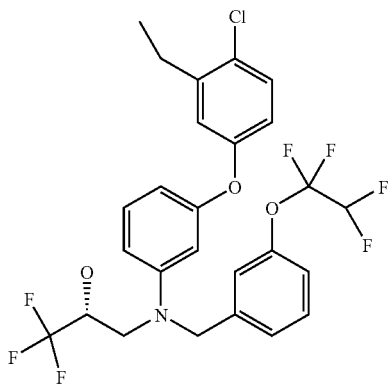

Drug 4 has a solubility in water of less than 1 µg/mL, and a Log P value of 10.0, as determined by the average value estimated using Crippen's, Viswanadhan's, and Broto's fragmentation methods. The $T_g$ of amorphous Drug 4 was determined by DSC analysis to be about −15° C. The solubility parameter of Drug 4 was calculated using the procedure outlined above to be 22.9 $(J/cm^3)^{1/2}$.

Drug 5 was 5-(2-(4-(3-benzisothiazolyl)-piperazinyl) ethyl-6-chlorooxindole, also known as ziprasidone, having the structure:

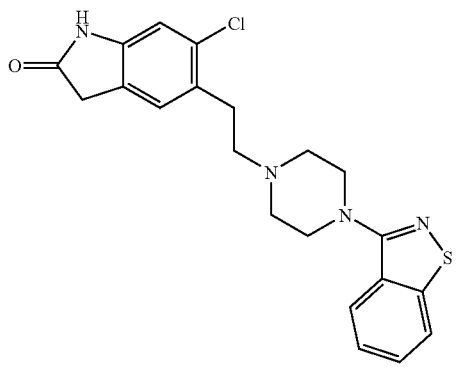

The free base form of Drug 5 has a solubility in water of less than 0.1 μg/mL, while the aqueous solubility of the HCl salt form is about 10 μg/mL. Drug 4 had a Log P value of 4.7, as determined by the average value estimated using Crippen's, Viswanadhan's, and Broto's fragmentation methods. The $T_g$ of amorphous Drug 5 (free base) was determined by DSC analysis to be about 72° C., and the $T_m$ (of the free base) is about 224° C. The solubility parameter of Drug 4 was calculated using the procedure outlined above to be 29.29 $(J/cm^3)^{1/2}$.

Drug 6 was 1-[4-ethoxy-3-(6,7-dihydro-1-methyl-7-oxo-3-propyl-1H-pyrazolo[4,3-d]pyrimidin-5-yl)phenylsulphonyl]-4-methylpiperazine citrate salt, also known as sildenafil citrate, having the structure:

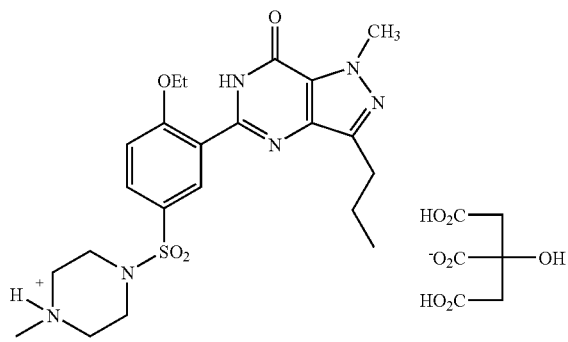

Drug 6 has a solubility in pH 6 buffer of about 20 μg/mL, and a Log P value of 1.98, as determined by the average value estimated using Crippen's, Viswanadhan's, and Broto's fragmentation methods. The $T_g$ of amorphous Drug 6 was determined by DSC analysis to be 84° C.

Drug 7 was quinoxaline-2-carboxylic acid [4(R)-carbamoyl-1(S)-3-fluorobenzyl)-2(S),7-dihydroxy-7-methyl-octyl] amide, having the structure:

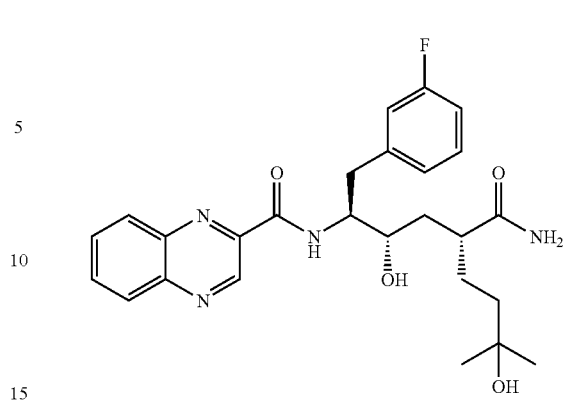

The free base form of Drug 7 has a solubility in water of about 330 μg/mL. Drug 7 has a Log P value of 2.0, as determined by the average value estimated using Crippen's, Viswanadhan's, and Broto's fragmentation methods. The $T_g$ of amorphous Drug 7 (free base) was determined by DSC analysis to be about 69° C., and the $T_m$ (of the free base) is about 165° C. The solubility parameter of Drug 7 was calculated using the procedure outlined above to be 30.14 $(J/cm^3)^{1/2}$. Drug 7 is an acid sensitive drug.

Synthesis of HPMCAS Polymers

Polymer 1, having the degree of substitution shown in Table 2, was synthesized using the following procedure. 100 mL of glacial acetic acid was added to a 250 mL round bottom flask equipped with a water condenser and a stir bar and placed into an oil bath set at 85° C. To this, 10.0367 g of HPMC (Dow E3 Prem LV, having a $DOS_M$ of 1.88 and a $DOS_{HP}$ of 0.25 according to the certificate of analysis provided by the manufacturer) and 10.1060 g of sodium acetate were added and allowed to dissolve. Once complete dissolution of the HPMC occurred, 1.1831 g of succinic anhydride was added and allowed to react for 2.5 hours. After which, an excess (41.362 g) of acetic anhydride was added and allowed to react for an additional 21 hours.

After a total reaction time of approximately twenty-four hours, the reaction mixture was quenched into about 700 mL of water, precipitating the polymer. The polymer was then isolated using a Buchner funnel and washed with 3×75 mL of additional water. Once isolated and fairly dry, the polymer was dissolved in about 150 mL of acetone and re-precipitated into about 500 mL of water. Lastly, the polymer was collected using a Buchner funnel and dried in vacuo to yield 9.2 g of an off-white solid. The degree of substitution of acetate and succinate on the polymer was determined using the procedures outlined above; the results are given in Table 2. The degree of substitution for methoxy and hydroxypropoxy were assumed to be unchanged from the certificate of analysis provided by the manufacturer of the HPMC starting material.

The solubility parameter for this polymer was determined using the group contribution methods of Barton, outlined above. The result of this calculation is given in Table 2. The $T_g$ of the polymer was also determined using a DSC at 50% RH and is included in Table 2.

Additional HPMCAS polymers were prepared with the degrees of substitution and $T_g$ values given in Table 2, using procedures similar to those described above, with the exceptions noted in Table 3. The solubility parameters were also calculated using the procedures described herein, and are given in Table 2. In addition, FIG. 1 shows a plot of $DOS_S$ versus $DOS_{Ac}$ for the inventive polymers.

TABLE 2

| Polymer | $DOS_{HP}$ | $DOS_M$ | $DOS_{Ac}$ | $DOS_S$ | $DOS_M$ + $DOS_{Ac}$ + $DOS_S$ | $DOS_{Ac}$ + $DOS_S$ | $T_g$ (° C. at 50% RH) | Solubility Parameter $(J/cm^3)^{1/2}$ |
|---|---|---|---|---|---|---|---|---|
| 1 | 0.25 | 1.91 | 0.70 | 0.25 | 2.86 | 0.95 | 102 | 21.74 |
| 2 | 0.25 | 1.88 | 0.76 | 0.24 | 2.88 | 1.00 | 91 | 21.68 |
| 3 | 0.25 | 1.91 | 0.79 | 0.20 | 2.90 | 0.99 | ND* | 21.47 |
| 4 | 0.25 | 1.91 | 0.77 | 0.19 | 2.87 | 0.96 | ND | 21.55 |
| 5 | 0.25 | 1.88 | 0.82 | 0.13 | 2.83 | 0.95 | 93 | 21.56 |
| 6 | 0.25 | 1.88 | 0.83 | 0.03 | 2.74 | 0.86 | 99 | 21.61 |

*ND = Not determined

TABLE 3

| Polymer | Starting Polymer Grade | Mass (g) | Succinic Anhydride Mass (g) | Succinic Anhydride Reaction Time (hr) | Acetic Anhydride Mass (g) | Acetic Anhydride Reaction Time (hr) |
|---|---|---|---|---|---|---|
| 1* | Shin Etsu HPMC-LV | 20.0491 | 4.7136 | 2.5 | 160.054 | 21.75 |
|    | | 20.0269 | 4.7173 | 2.5 | 160.221 | 21.75 |
| 2 | Dow E3 Prem LV | 10.0596 | 2.4166 | 5.75 | 67.4 | 23.75 |
| 3 | Shin Etsu HPMC-LV | 20.1101 | 3.3095 | 2.25 | 108.2 | 15.25 |
| 4 | Shin Etsu HPMC-LV | 20.1139 | 3.2132 | 2.25 | 108.2 | 17.25 |
| 5 | Dow E3 Prem LV | 10.10367 | 1.1831 | 2.5 | 41.362 | 21 |
| 6 | Dow E3 Prem LV | 10.0880 | 0.3824 | 18 | 40.0 | 5.75 |

*Two batches were synthesized to form one lot of polymer.

Synthesis of HPMCA Polymers

Polymer 7, having the degree of substitution shown in Table 4, was synthesized using the following procedure. About 50 mL of glacial acetic acid was added to a 250 mL round bottom flask equipped with a water condenser and a stir bar and placed into an oil bath set at 85° C. To this, 5.0031 g of HPMC (Dow E3 Prem LV, having a $DOS_M$ of 1.88 and a $DOS_{HP}$ of 0.25 according to the certificate of analysis provided by the manufacturer) and 5.0678 g of sodium acetate were added and allowed to dissolve. Once complete dissolution of the HPMC occurred, 1.530 g of acetic anhydride was added and the mixture was allowed to react for 7.75 hours.

The reaction mixture was quenched into about 800 mL of water saturated with sodium chloride, precipitating the polymer. The polymer was then filtered using a Buchner funnel and washed with hot water. The polymer was dried in vacuo to yield an off-white solid. The degree of acetate substitution on the polymer was determined using the procedures outlined above; the results are given in Table 4. The degree of substitution for methoxy and hydroxypropoxy were assumed to be unchanged from the certificate of analysis provided by the manufacturer of the HPMC starting material.

The solubility parameter for this polymer was determined using the group contribution methods of Barton, outlined above. The result of this calculation is given in Table 4. The $T_g$ of the polymer was also determined using a DSC at 0% and 50% RH and is included in Table 4. Also included in Table 4 are values for HPMC (Dow E3 Prem LV).

Additional HPMCA polymers were prepared with the degrees of substitution and $T_g$ values given in Table 4, using procedures similar to those described above, with the exceptions noted in Table 5. The solubility parameters were also calculated using the procedures described herein, and are given in Table 4.

TABLE 4

| Polymer | $DOS_{HP}$ | $DOS_M$ | $DOS_{Ac}$ | Total DOS* | $T_g$ (° C. at 0% RH) | $T_g$ (° C. at 50% RH) | Solubility Parameter $(J/cm^3)^{1/2}$ |
|---|---|---|---|---|---|---|---|
| 7 | 0.25 | 1.88 | 0.29 | 2.17 | 143 | 107 | 23.9 |
| 8 | 0.25 | 1.88 | 0.44 | 2.32 | 136 | 111 | 23.2 |
| 9 | 0.25 | 1.88 | 0.72 | 2.60 | 131 | 102 | 22.1 |
| 10 | 0.25 | 1.88 | 0.30 | 2.18 | 140 | ND** | 23.8 |
| 11 | 0.25 | 1.88 | 0.42 | 2.30 | ND | ND | 23.3 |
| 12 | 0.25 | 1.91 | 0.36 | 2.27 | 145 | 105 | 22.4 |
| 13 | 0.25 | 1.88 | 0.17 | 2.05 | 146 | 102 | 24.4 |
| 14 | 0.23 | 1.94 | 0.25 | 2.19 | ND | ND | 23.8 |
| 15 | 0.25 | 1.93 | 0.19 | 2.12 | ND | ND | 24.1 |
| 16 | 0.25 | 1.88 | 0.29 | 2.17 | 139 | 103 | 23.9 |
| 17 | 0.25 | 1.88 | 0.29 | 2.17 | 142 | ND | 23.9 |
| 18 | 0.25 | 1.88 | 0.42 | 2.30 | ND | ND | 23.3 |
| HPMC | 0.25 | 1.88 | 0 | 1.88 | 142 | 96 | 25.3 |

*Total DOS = $DOS_M$ + $DOS_{Ac}$
**ND = not determined

TABLE 5

| Polymer | Glacial acetic acid (mL) | Starting Polymer Grade | Starting Polymer Mass (g) | Acetic Anhydride Mass (g) | Reaction Time (hr) |
|---|---|---|---|---|---|
| 7 | 51.26 g | Dow E3 Prem LV | 5.0031 | 1.530 | 7.75 |
| 8 | 100 | Dow E3 Prem LV | 10.016 | 4.542 | 17.5 |
| 9 | 50 | Dow E3 Prem LV | 5.0025 | 3.031 | 7.42 |
| 10 | 300 | Dow E3 Prem LV | 30.009 | 9.21 | 10 |
| 11 | 300 | Dow E3 Prem LV | 30.069 | 13.68 | 11 |
| 12 | 150 | Shin Etsu HPMC-LV | 15.019 | 4.587 | 26 |
| 13 | 300 | Dow E3 Prem LV | 30.003 | 2.517 | 12 |
| 14 | 150 | Dow E50 Prem LV | 10.079 | 2.98 | 19 |
| 15 | 300 | Dow E10M Prem LV | 3.0220 | 1.81 | 19 |
| 16 | 300 | Dow E3 Prem LV | 30.003 | 9.2 | 12 |

TABLE 5-continued

| Polymer | Glacial acetic acid (mL) | Starting Polymer Grade | Starting Polymer Mass (g) | Acetic Anhydride Mass (g) | Reaction Time (hr) |
|---|---|---|---|---|---|
| 17 | 300 | Dow E3 Prem LV | 30.011 | 9.21 | 9 |
| 18 | 600 | Dow E3 Prem LV | 60.006 | 22.40 | 12 |

Formation of Solid Amorphous Dispersions

Dispersion 1

A solid amorphous dispersion of 50 wt % Drug 1 and 50 wt % Polymer 1 was prepared using a spray drying process as follows. A spray solution was prepared by dissolving 100 mg Drug 1 and 100 mg Polymer 1 in 35 gm of acetone. This solution was spray dried using a "mini" spray-dryer, which consisted of an atomizer in the top cap of a vertically oriented 11-cm diameter stainless steel pipe. The atomizer was a two-fluid nozzle (Spraying Systems Co. 1650 fluid cap and 64 air cap), where the atomizing gas was nitrogen delivered to the nozzle at 70° C. and a flow rate of 15 gm/min, and the solution to be spray dried was delivered to the nozzle at room temperature and a flow rate of 1.3 mL/min using a syringe pump. Filter paper with a supporting screen was clamped to the bottom end of the pipe to collect the solid spray-dried material and allow the nitrogen and evaporated solvent to escape. The spray drying parameters are summarized in Table 6.

Dispersions 2-13

Spray-dried dispersions were prepared using the procedure described for Dispersion 1 except that the drug and polymer were varied as noted in Table 6. For dispersions 1 to 11, the drug loading of the final dispersion was 50 wt %. For dispersions 12 and 13, the HCl salt form of Drug 5 was used; the drug loading of the final dispersion was 10 wt % Drug 5 (HCl salt form), or 9.2 wt % of active Drug 5.

TABLE 6

| Dispersion | Drug | Drug Mass (mg) | Polymer | Polymer Mass (mg) | Solvent | Solvent Mass (g) |
|---|---|---|---|---|---|---|
| 1 | Drug 1 | 100 | 1 | 100 | Acetone | 35 |
| 2 | Drug 1 | 1000 | 2 | 1000 | Acetone | 50 |
| 3 | Drug 1 | 1000 | 3 | 1000 | Acetone | 150 |
| 4 | Drug 1 | 499.8 | 6 | 400.4 | 2:1 Acetone:Methanol (w/w) | 20 |
| 5 | Drug 2 | 100 | 1 | 100 | Acetone | 15 |
| 6 | Drug 2 | 100 | 2 | 100 | Acetone | 15 |
| 7 | Drug 2 | 150 | 3 | 150 | Acetone | 30 |
| 8 | Drug 3 | 100 | 2 | 100 | Acetone | 15 |
| 9 | Drug 3 | 125 | 3 | 125 | Acetone | 30 |
| 10 | Drug 3 | 180 | 6 | 180 | 1:1 Acetone:Methanol (v/v) | 20 mL |
| 11 | Drug 4 | 100 | 4 | 100 | Acetone | 15 |
| 12 | Drug 5 (HCl) | 50 | 1 | 450 | Methanol | 25 |
| 13 | Drug 5 (HCl) | 50 | 3 | 450 | Methanol | 25 |
| Control 1 | Drug 1 | 20 | HPMCAS MF | 20 | Acetone | 16 |
| Control 2 | Drug 1 | 250 | HPMCAS HF | 250 | Acetone | 35 |
| Control 3 | Drug 2 | 100 | HPMCAS HF | 100 | Acetone | 20 |
| Control 4 | Drug 3 | 50 | HPMCAS MF | 50 | Acetone | 5 |
| Control 5 | Drug 3 | 50 | HPMCAS HF | 50 | Acetone | 5 |
| Control 6 | Drug 4 | 100 | HPMCAS-HG | 100 | Acetone | 15 |
| Control 7 | Drug 4 | 50 | HPMCAS-MG | 150 | Methanol | 20 |

Dispersions 14-16

Spray-dried dispersions were prepared using the procedure described for Dispersion 1 except that the drug and polymer were varied as noted in Table 7. For Dispersions 14, 14 and 16, the drug loading of the final dispersion was 50 wt %.

Dispersion 17

A solid amorphous dispersion of 50 wt % Drug 1 and 50 wt % Polymer 10 was prepared using a spray drying process as follows. Polymer 10 (6 gm) was added to 1000 mL of methanol to which was added 1000 mL of THF. The mixture was stirred and heated to near boiling for about 45 minutes, allowing the polymer to dissolve. The resulting mixture had a slight haze after the entire amount of polymer had been added. The mixture was allowed to cool to room temperature, and 6 gm of Drug 1 was added and dissolved with stirring. The spray solution was pumped using a high-pressure pump to a spray drier (a Niro type XP Portable Spray-Dryer with a Liquid-Feed Process Vessel ("PSD-1")), equipped with a pressure nozzle (Schlick 3.5). The PSD-1 was equipped with a 9-inch chamber extension to increase the residence time within the drier, which allowed the product to dry before reaching the angled section of the spray dryer. The spray drier was also equipped with a 316 SS circular diffuser plate with 1/16-inch drilled holes, having a 1% open area. This small open area directed the flow of the drying gas to reduce product recirculation within the spray dryer. The nozzle sat flush with the diffuser plate during operation. A Bran+Lubbe N-P31 high-pressure pump was used to deliver liquid to the nozzle. The pump was followed by a pulsation dampener to reduce pulsation at the nozzle. The spray solution was pumped to the spray drier at about 100 g/min at a pressure of 300 psig. Drying gas (e.g., nitrogen) was circulated through the diffuser plate at an inlet temperature of 130° C. The evaporated solvent and drying gas exited the spray drier at a temperature of 65° C. The resulting solid amorphous dispersion was collected in a cyclone, and post-dried in a vacuum desiccator.

Dispersion 18

Dispersion 18 was prepared using the procedure described for Dispersion 17 except that Polymer 11 was used as noted in Table 7. For Dispersion 18, the Drug 1 loading of the final dispersion was 50 wt %.

Dispersions 19-20

Spray-dried dispersions were prepared using the procedure described for Dispersion 1 except that the drug and polymer were varied as noted in Table 7. For Dispersions 19 and 20 the drug loading of the final dispersion was 75 wt % and 25 wt %, respectively. For Dispersion 19, the citrate salt form of Drug 6 was used. For Dispersion 20, the HCl salt form of Drug 5 was used.

Dispersion 21

Dispersion 21 was prepared using the procedure described for Dispersion 1 with the exceptions noted in Table 7. For Dispersion 21, the Drug 7 loading of the final dispersion was 50 wt %.

Control Dispersions 1-7

Control dispersions were prepared as noted in Table 6 using the method of Example 1 except that commercial grades of HPMCAS, available from Shin Etsu (Tokyo, Japan) were used as the dispersion polymers.

Control Dispersion 8

A control dispersion of Drug 5 (Control 8) was prepared as noted in Table 7 using the method outlined for Dispersion 1 except that the commercial grade of HPMC, E3 Prem LV, available from Dow Chemical Company (Midland, Mich.) was used as the dispersion polymer.

Control 9

A control dispersion of Drug 7 (Control 7) was prepared as noted in Table 7 using the method outlined for Dispersion 1 except that HPMCAS-LF (Shin Etsu AQOAT-LF, Tokyo, Japan) was used as the dispersion polymer.

Example 1

In Vitro Evaluation of Concentration Enhancement

Dispersions 2, 3, 4, and 10 were evaluated in in vitro dissolution tests using a microcentrifuge method. In this method, 3.6 mg of the spray-dried dispersions was added to a 2-mL microcentrifuge tube. The tube was placed in a 37° C. sonicating bath, and 1.8 mL of phosphate-buffered saline (PBS) at pH 6.5 and 290 mOsm/kg was added. The samples were quickly mixed using a vortex mixer for about 90 seconds. The theoretical maximum concentration of drug if all the drug dissolved was 1000 µg/mL. The samples were centrifuged at 13,000 G at 37° C. for 1 minute. The resulting supernatant solution was then sampled (100 µL) and diluted with 200 µL methanol and then analyzed by HPLC. The tubes were then mixed on the vortex mixer and allowed to stand undisturbed at 37° C. until the next sample. Samples were collected at 4, 10, 20, 40, 90, and 1200 minutes.

As controls, in vitro tests were performed using the procedure described above, except that 0.18 mg of crystalline drug was placed in a microcentrifuge tube and mixed with 1.8 mL of PBS.

TABLE 7

| Dispersion | Drug | Drug Mass (mg) | Polymer | Polymer Mass (mg) | Solvent | Solvent amount |
|---|---|---|---|---|---|---|
| 14 | Drug 1 | 181 mg | 7 | 181 mg | 1:1 Methanol:THF (v/v) | 50 mL |
| 15 | Drug 1 | 230.4 mg | 8 | 230.4 mg | 3:1 Methanol:EtOAc | 28.8 g |
| 16 | Drug 1 | 177 mg | 9 | 177 mg | Acetone | 18 mL |
| 17 | Drug 1 | 6.0141 g | 10 | 6.0143 g | 1:1 Methanol:THF (v/v) | 2 L |
| 18 | Drug 1 | 6.5063 g | 11 | 6.5063 g | 1:1 Methanol:THF (v/v) | 2 L |
| 19 | Drug 6 (citrate) | 450 mg | 17 | 150 mg | 95:5 Methanol:H$_2$O | 81 g |
| 20 | Drug 5 (HCl) | 125 mg | 18 | 375 mg | 95:5 Methanol:H$_2$O | 50 g |
| 21 | Drug 7 | 2450 mg | 16 | 2450 mg | 80:20 Methanol:H$_2$O | 93.1 g |
| Control 8 | Drug 5 (HCl) | 125 mg | HPMC | 375 mg | 95:5 Methanol:H$_2$O | 50 g |
| Control 9 | Drug 7 | 50 mg | HPMCAS-LF | 150 mg | Methanol | 40 g |

The results of these dissolution tests are summarized in Table 8, which shows the maximum concentration of drug in solution during the first 90 minutes of the test (MDC$_{90}$), the area under the aqueous concentration versus time curve after 90 minutes (AUC$_{90}$), and the concentration at 1200 minutes (C$_{1200}$).

TABLE 8

| Dispersion | Drug | Polymer | MDC$_{90}$ (µg/mL) | AUC$_{90}$ (min-µg/mL) | C$_{1200}$ (µg/mL) |
|---|---|---|---|---|---|
| 2 | Drug 1 | 2 | 42 | 1,100 | 3 |
| 3 | Drug 1 | 3 | 31 | 1,900 | 35 |
| 4 | Drug 1 | 6 | 39 | 1,600 | 5 |
| Crystalline Drug 1 | Drug 1 | — | <1 | <88 | <1 |
| 10 | Drug 3 | 6 | 68 | 800 | 11 |
| Crystalline Drug 3 | Drug 3 | — | <1 | <88 | <1 |

The results in Table 8 show that the dispersions of the present invention show concentration enhancement over the crystalline control. For Drug 1, Dispersions 2, 3, and 4 provided MDC$_{90}$ values that were greater than 42-fold, 31-fold, and 39-fold that provided by the crystalline control, and AUC$_{90}$ values that were greater than 12.5-fold, 21.6-fold, and 18.2-fold that provided by the crystalline control, respectively. For Drug 3, Dispersion 10 provided a MDC$_{90}$ value that was greater than 68-fold that provided by the crystalline control, and an AUC$_{90}$ value that was greater than 9-fold that provided by the crystalline control.

Example 2

In Vivo Tests

Dispersions 1 and 4 were used as oral powders for constitution (OPC) for evaluating the performance of the dispersions in in vivo tests using male beagle dogs. The OPC was dosed as a suspension in a solution containing 0.5 wt % hydroxypropyl cellulose METHOCEL® (from Dow Chemical Co.), and was prepared as follows. First, 7.5 g of METHOCEL® was weighed out and added slowly to approximately 490 ml of water at 90-100° C. to form a METHOCEL® suspension. After all the METHOCEL® was added, 1000 mL of cool/room temperature water was added to the suspension, which was then placed in an ice water bath. When all of the METHOCEL® had dissolved, 2.55 g of polyoxyethylene 20 sorbitan monooleate (TWEEN 80) were added and the mixture stirred until the TWEEN 80 had dissolved, thus forming a stock suspension solution.

To form the OPC, sufficient quantity of the test composition to result in a 90 mgA amount of Drug 1 was accurately weighed and placed into a mortar. ("mgA" refers to mg of active drug.) A 20 mL quantity of the stock suspension solution was added to the mortar and the test composition was mixed with a pestle. Additional METHOCEL® suspension was added gradually with mixing until a total of 400 mL of the stock suspension solution had been added to the mortar. The suspension was then transferred to a flask, thus forming the OPC. This process was repeated for each of Dispersions 1 and 4. In addition, an OPC containing 90 mgA of amorphous Drug 1 was prepared using the same procedure.

Six male beagle dogs were each dosed with the OPC. On the day of the study, the dogs in either a fasted state or in the fed state (50 gm dog chow) were dosed with the OPC using a gavage tube and a syringe. Blood was collected from the jugular vein of the dogs before dosing and at various time points after dosing. To 100 µL of each plasma sample, 5 mL of methyl-tert-butyl ether (MTBE) and 1 mL of 500 mM sodium carbonate buffer (pH 9) were added; the sample was vortexed for 1 minute and then centrifuged for 5 minutes. The aqueous portion of the sample was frozen in a dry-ice/acetone bath, and the MTBE layer was decanted and evaporated in a vortex evaporator. Dried samples were reconstituted in 100 µL of mobile phase (33% acetonitrile and 67% of 0.1% formic acid in water). Analysis was carried out by HPLC.

The results of these tests are presented in Table 9 and show that the compositions of the present invention provided enhanced drug concentration and relative bioavailability relative to the amorphous Drug 1 control. In the fasted state, the dispersions of the present invention provided concentration enhancement relative to the amorphous drug alone. Indeed, the amorphous drug showed virtually no exposure in the fasted state, while the dispersions of the present invention showed the C$_{max}$ and AUC$_{0-12}$ values shown in Table 9. In the fed state, Dispersion 1 provided a C$_{max}$ that was 6.5-fold that of amorphous Drug 1, and an AUC$_{0-12}$ that was 7.3-fold that of amorphous Drug 1.

TABLE 9

| Composition | Drug Loading (wt %) | Polymer | Fed State | C$_{max}$ (ng/ml) | AUC$_{(0-12)}$ (ng-hr/mL) |
|---|---|---|---|---|---|
| Dispersion 1 | 50 | 1 | Fasted | 580 ± 210 | 2350 ± 890 |
| Dispersion 4 | 50 | 6 | Fasted | 180 ± 70 | 570 ± 240 |
| Amorphous Drug 1 | 100 | — | Fasted | 0 | 0 |
| Dispersion 1 | 50 | 1 | Fed | 1240 ± 410 | 4690 ± 820 |
| Amorphous Drug 1 | 100 | — | Fed | 190 ± 55 | 640 ± 240 |

Example 3

Evaluation of Solubility of Drug in Polymers

The solubilities of drug in HPMCAS polymers were determined using a double-scan differential scanning calorimetry (DSC) analysis of the dispersions as follows. The DSC analysis was carried out on either a TA Instruments DSC2920 or a Mettler DSC 821, calibrated with indium. DSC samples were prepared by weighing 2-4 mg of the dispersion in an aluminum pan with a pinhole. The sample was heated under nitrogen, at a rate of 5° C. per minute from about –20° C. to about 140° C. This analysis typically showed a single T$_g$ for the dispersion that was significantly higher than the T$_g$ for pure amorphous drug. Heating above the T$_g$ allows the drug to phase separate from the dispersion if the drug solubility in the polymer is lower than the drug loading.

The sample was then cooled and the sample was scanned a second time using the procedures outlined above. If the solubility of drug in the polymer was lower than the concentration of drug in the dispersion, the second scan showed two T$_g$s—one for phase separated amorphous drug and one for a low-drug-loading dispersion (corresponding to the loading of drug that is equal to the solubility of the drug in the polymer). The amount of phase separated amorphous drug was estimated by comparing the magnitude of the heat capacity for the phase separated amorphous drug with the heat capacity for pure amorphous drug controls. From these data, the solubility of drug in the polymer was determined. Table 10 summarizes the results of these tests.

TABLE 10

| Dispersion | Drug | Polymer | $(\delta_D-\delta_P)^2$ (J/cm³) | Estimated Solubility of Drug in Polymer from Double-Scan DSC (wt %) |
|---|---|---|---|---|
| 1 | 1 | 1 | 1.2 | 41 |
| 2 | 1 | 2 | 1.0 | 43 |
| 3 | 1 | 3 | 0.7 | >50 |
| 4 | 1 | 6 | 0.9 | >75 |
| Control 1 | 1 | HPMCAS MF | 2.6 | 25-30 |
| Control 2 | 1 | HPMCAS HF | 1.8 | 35-40 |
| 5 | 2 | 1 | 1.9 | 32 |
| 6 | 2 | 2 | 1.8 | 36 |
| 7 | 2 | 3 | 1.3 | 44 |
| Control 3 | 2 | HPMCAS HF | 2.7 | 29 |
| 8 | 3 | 2 | 1.5 | 36 |
| 9 | 3 | 3 | 1.0 | 43 |
| 10 | 3 | 6 | 1.3 | >50 |
| Control 4 | 3 | HPMCAS MF | 3.3 | 21 |
| Control 5 | 3 | HPMCAS HF | 2.4 | 25 |
| 11 | 4 | 4 | 1.4 | >50 |
| Control 6 | 4 | HPMCAS-HG | 0.9 | >50 |
| Control 7 | 4 | HPMCAS-MG | 0.7 | 15-25 |

These data show that for Drug 1, Drug 2, and Drug 3, the smaller the difference in solubility parameter between the drug and polymer, $(\delta_D-\delta_P)^2$, the higher the solubility of drug in the polymer.

The results for Drug 4 do not follow this trend. This is believed to be because the calculation of the solubility parameter for Drug 4 is not accurate due to the high Log P of this drug (about 10). It is believed that the actual solubility parameter for Drug 4 is lower than the calculated value of 22.9 $(J/cm^3)^{1/2}$. In any case, the data show that the solubility of Drug 4 in the HPMCAS of the present invention is higher than it is for the commercial M grade.

Example 4

Demonstration of Improved Physical Stability

To demonstrate the improvement in physical stability obtained with the HPMCAS polymers of the present invention, samples of Dispersion 1 and Control 2 were placed into a controlled temperature and humidity oven at the conditions given in Table 11 for 6 weeks. Following storage at these conditions, the dispersions were analyzed by DSC using the procedures outlined in Example 3. From the initial scan, the amount of phase-separated drug was estimated from the heat capacity—the results are given in Table 11. Also given in Table 11 is the rate of phase separation of drug obtained by dividing the amount of phase-separated drug by 6 weeks.

TABLE 11

| | Storage for 6 weeks at 40° C./75% RH | | Storage for 6 weeks at 40° C./25% RH | |
|---|---|---|---|---|
| Dispersion | Drug Phase Separated (wt %) | Rate of Phase Separation (wt %/week) | Drug Phase Separated (wt %) | Rate of Phase Separation (wt %/week) |
| 1 | 18.6 | 3.1 | 8.7 | 1.5 |
| Control 2 | 30 | 5.0 | 15 | 2.5 |
| Relative Degree of Improvement in Physical Stability | — | 1.6 | — | 1.7 |

The data in Table 11 show that the rate of phase separation was slower when the dispersions were stored under drier conditions (40° C./25% RH vs. 40° C./75% RH). The dispersion of the present invention provided a relative degree of improvement in physical stability of 1.6 relative to the control dispersion.

Example 5

Demonstration of Crystallization Inhibition

The HPMCAS polymers of the present invention were demonstrated to inhibit drug crystallization in the following test. First, Dispersions 12 and 13 were evaluated in an in vitro dissolution test using the microcentrifuge method described in Example 1 except that 2.04 mg of the dispersions were separately added to microcentrifuge tubes in duplicate. A 1.8-mL sample of a model fasted duodenal (MFD) solution was then added to the tube and the samples were quickly mixed using a vortex mixer for about 90 seconds. The theoretical maximum concentration of drug if all the drug dissolved was about 100 µgA/mL, where "µgA" refers to the active micrograms of Drug 5. Samples were collected and analyzed by HPLC using a Kromasil $C_4$ column (250 mm×4.6 mm). The mobile phase consisted of 0.2 vol % $H_3PO_4$/acetonitrile in a volume ratio of 45/55. Drug concentration was calculated by comparing UV absorbance at 245 nm to the absorbance of Drug 5 standards.

As a control, 3.6 mgA of Drug 5 (in the HCl salt form) was added to a separate microcentrifuge tube so that the concentration of drug if all of the drug had dissolved would have been about 200 µgA/mL. The results, summarized in Table 12, demonstrate that solid amorphous dispersions of Drug 5 and the polymers of the present invention show concentration enhancement as well as crystallization inhibition. The $MDC_{90}$ values provided by Dispersions 12 and 13 were 3.5-fold and 3.0-fold that of the crystalline Drug 5 control, while the $AUC_{90}$ values were 2.6-fold and 2.7-fold that of the crystalline control. Furthermore, the concentration of dissolved Drug 5 after 1200 minutes ($C_{1200}$) was higher for Dispersions 12 and 13 than the crystalline control, with Dispersions 12 and 13 providing $C_{1200}$ values that were 1.7- and 1.4-fold that of the crystalline control, respectively.

TABLE 12

| Dispersion | Drug | Polymer | $MDC_{90}$ (µg/mL) | $AUC_{90}$ (min-µg/mL) | $C_{1200}$ (µg/mL) |
|---|---|---|---|---|---|
| 12 | 5 (HCl salt) | 1 | 77 | 4,500 | 15 |
| 13 | 5 (HCl salt) | 3 | 67 | 4,600 | 13 |
| Crystalline Drug 5 | 5 (HCl salt) | — | 22 | 1,700 | 9 |

Example 6

In Vitro Evaluation of Concentration Enhancement

Dispersion 14 was evaluated in vitro using a membrane permeation test as follows. An Accurel® PP 1E microporous polypropylene membrane was obtained from Membrana GmbH (Wuppertal, Germany). The membrane was washed in isopropyl alcohol and rinsed in methanol in a sonicating bath for 1 minute at ambient temperature, and then allowed to air dry at ambient temperature. The feed side of the membrane was then plasma-treated to render it hydrophilic by placing a sample of the membrane in a plasma chamber. The atmosphere of the plasma chamber was saturated with water vapor at a pressure of 550 mtorr. A plasma was then generated using radio frequency (RF) power inductively coupled into the chamber via annular electrodes at a power setting of 50 watts for 45 seconds. The contact angle of a drop of water placed on the surface of the plasma-treated membrane was about 40°. The contact angle of a drop of water placed on the permeate side of the same membrane was greater than about 110°.

A permeate reservoir was formed by gluing a sample of the plasma-treated membrane to a glass tube having an inside diameter of about 1 inch (2.54 cm) using an epoxy-based glue (LOCTITE® E-30CL HYSOL® from Henkel Loctite Corp, Rocky Hill, Conn.). The feed-side of the membrane was oriented so that it was on the outside of the permeate reservoir, while the permeate-side of the membrane was oriented so that it was on the inside of the reservoir. The effective membrane area of the permeate reservoir was about 4.9 cm$^2$. The permeate reservoir was placed into a glass feed reservoir. The feed reservoir was equipped with a magnetic stir bar and the reservoir was placed on a stir plate and the stir rate was set to 100 rpm during the test. The apparatus was placed into a chamber maintained at 37° C. for the duration of the test. Further details of the test apparatus and protocols are presented in co-pending U.S. Provisional Patent Application Ser. No. 60/557,897, entitled "Method and Device for Evaluation of Pharmaceutical Compositions," filed Mar. 30, 2004, incorporated herein by reference.

To form the feed solution, a 1.2 mg sample of the dispersion was weighed into the feed reservoir. To this was added 5 mL of MFD solution previously described, consisting of PBS solution containing 7.3 mM sodium taurocholic acid and 1.4 mM of 1-palmitoyl-2-oleyl-sn-glycero-3-phosphocholine (0.5% NaTC/POPC). The concentration of Drug 1 in the feed solution would have been 120 μg/mL, if all of the drug had dissolved. The feed solution was mixed using a vortex mixer for 1 minute. Before the membrane contacted the feed solution, 5 mL of 20 wt % decanol in decane was placed into the permeate reservoir. Time zero in the test was when the membrane was placed in contact with the feed solution. A 50 μL aliquot of the permeate solution was collected at the times indicated. Samples were then diluted in 250 μL IPA and analyzed using HPLC.

As a control, 0.6 mg of crystalline Drug 1 (C1A) alone was added so that the concentration of drug would have been 120 μgA/mL, if all of the drug had dissolved.

The maximum flux of drug across the membrane (in units of μg/cm$^2$-min) was determined by performing a least-squares fit to the data from 0 to 60 minutes to obtain the slope, multiplying the slope by the permeate volume (5 mL), and dividing by the membrane area (4.9 cm$^2$). The results of this analysis are summarized in Table 13, and show that Dispersion 14 provided a maximum flux of Drug 1 through the membrane that was 1.3-fold that provided by crystalline drug, indicating that the dispersion made using Polymer 7 provided concentration enhancement of Drug 1 in the aqueous feed solution.

TABLE 13

| Dispersion | Formulation | Feed Solution | Maximum Flux of Drug 1 (μg/cm$^2$-min) |
|---|---|---|---|
| 14 | 50:50 Drug 1:Polymer 7 | 0.5% NaTC/POPC | 0.097 |
| Crystalline Drug 1 | Crystalline Drug 1 | 0.5% NaTC/POPC | 0.076 |

The in vitro membrane-permeation tests was performed using Dispersions 15, 17, and 18 using the procedures outlined above, except that the feed solution was designed to model the fed state, and consisted of PBS solution containing 29.2 mM sodium taurocholic acid and 5.6 mM of 1-palmitoyl-2-oleyl-sn-glycero-3-phosphocholine (2% NaTC/POPC). Control C1A was also tested under these conditions.

The maximum flux of drug across the membrane was calculated from the data using the procedures described above, and the results are presented in Table 14. These data show that the dispersions of Drug 1 and the HPMCA polymers of the present invention provided concentration enhancement for Drug 1 in the feed solution relative to the crystalline control. Dispersions 15, 17, and 18 provided maximum fluxes that were 1.5-fold, 4.7-fold, and 2.8-fold that of the crystalline control, respectively.

TABLE 14

| Dispersion | Formulation | Feed Solution | Maximum Flux of Drug 1 (μg/cm$^2$-min) |
|---|---|---|---|
| 15 | 50:50 Drug 1:Polymer 8 | 2.0 wt % NaTC/POPC | 0.20 |
| 17 | 50:50 Drug 1:Polymer 10 | 2.0 wt % NaTC/POPC | 0.61 |
| 18 | 50:50 Drug 1:Polymer 11 | 2.0 wt % NaTC/POPC | 0.36 |
| Crystalline Drug 1 | Crystalline Drug 1 | 2.0 wt % NaTC/POPC | 0.13 |

Example 7

In Vitro Evaluation of Concentration Enhancement

Dispersion 19 (75:25 Drug 6:Polymer 17) was evaluated in vitro using the membrane permeation test described for Example 6, except that the permeate solution consisted of 60 wt % decanol in decane. The feed solution was made using MFD solution (0.5% NaTC/POPC). The concentration of Drug 6 in the feed solution would have been 500 μg/mL (354 μgA/mL), if all of the drug had dissolved As a control, crystalline Drug 6 alone was used. The concentration of drug added would have been 354 μgA/mL Drug 6, if all of the drug had dissolved.

The maximum flux of drug across the membrane (in units of μg/cm$^2$-min) was determined from the data by estimating the tangent to the concentration versus time curve at time 0. The results are summarized in Table 15, and show that Dispersion 19 of Drug 6 and Polymer 17 provided concentration enhancement, providing a maximum flux of Drug 6 that was about 1.5-fold that of the crystalline control.

TABLE 15

| Sample | Formulation | Feed Solution | Maximum Drug Flux (μg/cm$^2$-min) |
|---|---|---|---|
| Dispersion 19 | 75:25 Drug 6:Polymer 17 | 0.5% NaTC/POPC | 5.8 |
| Crystalline Drug 6 | Crystalline Drug 6 | 0.5% NaTC/POPC | 3.8 |

Example 8

In Vitro Evaluation of Concentration Enhancement

Dispersion 19 was also evaluated in a microcentrifuge dissolution test using the following procedures. For this test, 1.7 mg of Dispersion 19 and 1.27 mg of Crystalline Drug 6 was added to respective microcentrifuge tubes. The tubes were placed in a 37° C. temperature-controlled bath, and 1.8 mL phosphate buffered saline (PBS) at pH 6.5 and 290 mOsm/kg containing 7.3 mM sodium taurocholic acid and 1.4 mM of 1-palmitoyl-2-oleyl-sn-glycero-3-phosphocholine was added to each tube. The concentration of Drug 6 would have been 500 mgA if all of the drug had dissolved. The samples were quickly mixed using a vortex mixer for about 60 seconds. The samples were centrifuged at 13,000 G at 37° C. for 1 minute. The resulting supernatant solutions were then sampled and diluted 1:6 (by volume) with methanol and then analyzed by high-performance liquid chromatography (HPLC). The contents of the tubes were mixed on the vortex mixer and allowed to stand undisturbed at 37° C. until the next sample was taken. Samples were collected at 4, 10, 20, 40, 90, and 1200 minutes.

The concentrations of Drug 6 obtained in these samples were used to determine the values of the maximum drug concentration between 0 and 90 minutes ($MDC_{90}$) and the area under the curve from 0 to 90 minutes ($AUC_{90}$). The results are shown in Table 16.

TABLE 16

| Sample | $MDC_{90}$ (μgA/mL) | $AUC_{90}$ (min * μgA/mL) |
|---|---|---|
| Dispersion 19 | 418 | 18,000 |
| Crystalline Drug 6 | 98 | 7,000 |

As can be seen from the data, Dispersion 19 provided concentration enhancement of Drug 6 relative to crystalline Drug 6. The $MDC_{90}$ provided by Dispersion 19 was 4.3-fold that of the crystalline drug, while the $AUC_{90}$ was 2.6-fold that of crystalline drug.

Example 9

In Vitro Evaluation of Concentration Enhancement

Dispersion 20 (25:75 Drug 5:Polymer 18) was evaluated in vitro using the membrane permeation test as described in Example 7. A control dispersion of Drug 5 (Control 8) (25:75 Drug 5:HPMC E3 Prem) was also tested for comparison. The concentration of Drug 5 in the feed solutions would have been 100 μg/mL (88 μgA/mL), if all of the drug had dissolved.

As another control crystalline Drug 5 alone was used. The concentration of drug added would have been 88 μgA/mL Drug 5, if all of the drug had dissolved.

The maximum flux of Drug 5 across the membrane was calculated from the data using the procedures described in Example 6, and the results are presented in Table 17. These data show that Dispersion 20 of Drug 5 and the HPMCA polymer of the present invention provided concentration enhancement relative to the crystalline control, with Dispersion 20 providing a maximum flux value that was about 1.4-fold that of the crystalline control (C5A). In addition, the data show that a dispersion made from HPMC (Control 8) did not provide concentration enhancement relative to the crystalline control. These data show that the HPMCA polymers of the present invention provide improvement over dispersions made using HPMC.

TABLE 17

| Dispersion | Formulation | Feed Solution | Maximum Drug Flux (μg/cm²-min) |
|---|---|---|---|
| 20 | 25:75 Drug 5:Polymer 18 | 0.5% NaTC/POPC | 0.22 |
| Control 8 | 25:75 Drug 5:HPMC | 0.5% NaTC/POPC | 0.10 |
| Crystalline Drug 1 | Crystalline Drug 5 | 0.5% NaTC/POPC | 0.16 |

Example 10

In Vivo Tests

Dispersion 17, consisting of 50:50 Drug 1:HPMCA Polymer 10, was dosed in male beagle dogs as an oral powder for constitution (OPC), by suspending the dispersion in a solution containing 0.5 wt % hydroxypropyl cellulose METHOCEL® (from Dow Chemical Co.), as follows. First, 7.5 g of METHOCEL® was weighed out and added slowly to approximately 490 ml of water at 90-100° C. to form a METHOCEL® suspension. After all the METHOCEL® was added, 1000 mL of cool/room temperature water was added to the suspension, which was then placed in an ice water bath. When all of the METHOCEL® had dissolved, 2.55 g of polyoxyethylene 20 sorbitan monooleate (TWEEN 80) were added and the mixture stirred until the TWEEN 80 had dissolved, thus forming a stock suspension solution.

To form the OPC, sufficient quantity of the test composition to result in a 90 mgA amount of Drug 1 was accurately weighed and placed into a mortar. A 20 mL quantity of the stock suspension solution was added to the mortar and the test composition was mixed with a pestle. Additional METHOCEL® suspension was added gradually with mixing until a total of 400 mL of the stock suspension solution had been added to the mortar. The suspension was then transferred to a flask, thus forming the OPC. In addition, an OPC containing 90 mgA of amorphous Drug 1 was prepared using the same procedure.

Six male beagle dogs were each dosed with the OPC. On the day of the study, the dogs in either a fasted state or in the fed state (50 gm dog chow) were dosed with the OPC using a gavage tube and a syringe. Blood was collected from the jugular vein of the dogs before dosing and at various time points after dosing. To 100 μL of each plasma sample, 5 mL of methyl-tert-butyl ether (MTBE) and 1 mL of 500 mM sodium carbonate buffer (pH 9) were added; the sample was vortexed for 1 minute and then centrifuged for 5 minutes. The aqueous portion of the sample was frozen in a dry-ice/acetone bath, and the MTBE layer was decanted and evaporated in a vortex evaporator. Dried samples were reconstituted in 100 μL of mobile phase (33% acetonitrile and 67% of 0.1% formic acid in water). Analysis was carried out by HPLC.

The results of these tests are presented in Table 18 and show that the composition of the present invention provided enhanced drug concentration and relative bioavailability relative to the amorphous Drug 1 control. In the fasted state, the dispersion of the present invention provided concentration enhancement relative to amorphous drug alone. Indeed, the amorphous drug showed virtually no exposure in the fasted state, while the dispersion of the present invention showed the $C_{max}$ and $AUC_{0-12}$ values shown in Table 18. In the fed state, Dispersion 17 provided a $C_{max}$ that was 3.9-fold that of amorphous Drug 1, and an $AUC_{0-12}$ that was 3.4-fold that of amorphous Drug 1.

TABLE 18

| Composition | Drug Loading (wt %) | Polymer | Fed State | $C_{max}$ (ng/ml) | $AUC_{(0-12)}$ (ng-hr/mL) |
|---|---|---|---|---|---|
| Dispersion 17 | 50 | 10 | Fasted | 236 ± 101 | 559 ± 268 |
| Amorphous Drug 1 | 100 | — | Fasted | 0 | 0 |
| Dispersion 17 | 50 | 10 | Fed | 739 ± 207 | 2186 ± 283 |
| Amorphous Drug 1 | 100 | — | Fed | 190 ± 55 | 640 ± 240 |

Example 11

Evaluation of Chemical Stability

The chemical stability of Dispersion 21 (Drug 7 and HPMCA Polymer 16) and Control 9 (Drug 7 and HPMCAS-LF) was assessed by monitoring the potency of the drug before and after exposure to increased temperatures and relative humidity (RH) in accelerated-aging studies. Dispersions 21 and Control 9 were stored in a chamber maintained at 40° C. and 75% RH. Potencies of the dispersions before and after storage were determined using HPLC. A Kromasil C4 HPLC column was used with a mobile phase of 45 vol % of 0.2 vol % $H_3PO_4$, and 55 vol % acetonitrile. UV detection was measured at 245 nm. Drug 7 potency was the percent of the total HPLC peak area corresponding to the theoretical amount of drug originally present in the dispersion prior to storage based on the amount of drug present in the initial solutions before spray-drying. The results are shown in Table 19.

TABLE 19

| Dispersion | Composition | Storage Condition | Storage Time (days) | Drug 7 Potency (wt %) | Degree of Degradation (wt %) |
|---|---|---|---|---|---|
| 21 | 50 wt % Drug 7 in HPMCA Polymer 16 | 40° C./75% RH | 0 21 | 97.9 96.2 | 1.7 |
| Control 9 | 25% Drug 7 in HPMCAS-LF | 40° C./75% RH | 0 14 | 94.0 <1 | >93 |

The data in Table 19 show that when the acid-sensitive Drug 7 is dispersed in an acidic polymer, such as HPMCAS-LF, the drug rapidly degrades. When dispersed in the neutral polymer of the present invention, the drug maintained a high potency, showing a relative degree of improvement in chemical stability of greater than 54 (93÷1.7) after 21 days storage at 40° C./75% RH.

Example 12

In Vitro Evaluation of Concentration Enhancement

A physical mixture of 75 wt % Drug 6 and 25 wt % HPMCA Polymer 16 was evaluated using the microcentrifuge dissolution test described in Example 8. The concentration of Drug 6 would have been 500 μgA/mL if all of the drug had dissolved. A control consisting of a physical mixture of 75 wt % Drug 6 and 25 wt % HPMC (Dow E3 Prem LV) was tested in the same test.

The concentrations of Drug 6 obtained in these samples were used to determine the values of the maximum drug concentration between 0 and 90 minutes ($MDC_{90}$) and the area under the curve from 0 to 90 minutes ($AUC_{90}$). The results are shown in Table 20.

TABLE 20

| Sample | $MDC_{90}$ (μgA/mL) | $AUC_{90}$ (min * μgA/mL) |
|---|---|---|
| Physical Mixture of Drug 6 and Polymer 16 | 440 | 14,100 |
| Control (Physical Mixture Drug 6 and HPMC) | 258 | 8,600 |
| Crystalline Drug 6 | 98 | 7,000 |

As can be seen from the data, the physical mixture of Drug 6 with the HPMCA Polymer 16 of the present invention provided concentration enhancement of Drug 6 relative to a control physical mixture of Drug 6 and HPMC and relative to crystalline Drug 6. The $MDC_{90}$ provided by the composition of the present invention was 1.7-fold that of the physical mixture with HPMC and 4.5-fold that of the crystalline drug. The $AUC_{90}$ provided by the composition of the present invention was 1.6-fold that of the physical mixture with HPMC and 2.0-fold that of the crystalline drug.

The terms and expressions which have been employed in the foregoing specification are used therein as terms of description and not of limitation, an there is no intention, in the use of such terms and expressions, of excluding equivalents of the features shown and described or portions thereof, it being recognized that the scope of the invention is defined and limited only by the claims which follow.

The invention claimed is:

1. A composition comprising a drug and a polymer, wherein said polymer is hydroxypropyl methyl cellulose acetate (HPMCA), and wherein the degree of substitution of acetyl groups ($DOS_{Ac}$) on said HPMCA is at least 0.15.

2. The composition of claim 1 wherein said $DOS_{Ac}$ is less than or equal to 0.6.

3. The composition of claim 2 wherein said $DOS_{Ac}$ ranges from 0.2 to 0.5.

4. The composition of claim 3 wherein said $DOS_{Ac}$ ranges from 0.25 to 0.45.

5. The composition of claim 4 wherein said HPMCA has a solubility parameter of about 24.0 $(J/cm^3)^{1/2}$ or less.

6. The composition of claim 1 wherein the degree of substitution of methyl groups ($DOS_M$) on said polymer is equal to or greater than 1.6 and less than or equal to 2.15.

7. The composition of claim 1 wherein said drug is a low-solubility drug.

8. The composition of claim 7 wherein said composition comprises a solid amorphous dispersion comprising said low-solubility drug and said polymer.

9. The composition of claim 7 wherein said composition comprises a physical mixture of said low-solubility drug and said polymer.

* * * * *